United States Patent
Piché et al.

(10) Patent No.: US 9,721,326 B2
(45) Date of Patent: Aug. 1, 2017

(54) METHOD AND SYSTEM FOR IMPROVING RESOLUTION IN LASER IMAGING MICROSCOPY

(71) Applicant: UNIVERSITÉ LAVAL, Québec (CA)

(72) Inventors: Michel Piché, Québec (CA); Harold Dehez, Québec (CA); Yves De Koninck, Québec (CA)

(73) Assignee: UNIVERSITÉ LAVAL (CA)

( * ) Notice: Subject to any disclaimer, the term of this patent is extended or adjusted under 35 U.S.C. 154(b) by 109 days.

(21) Appl. No.: 14/356,555

(22) PCT Filed: Nov. 8, 2012

(86) PCT No.: PCT/CA2012/050794
§ 371 (c)(1),
(2) Date: May 6, 2014

(87) PCT Pub. No.: WO2013/067643
PCT Pub. Date: May 16, 2013

(65) Prior Publication Data
US 2014/0321772 A1    Oct. 30, 2014

(51) Int. Cl.
*G06K 9/00* (2006.01)
*G06T 3/40* (2006.01)
(Continued)

(52) U.S. Cl.
CPC ........ *G06T 3/4053* (2013.01); *G01N 21/6458* (2013.01); *G02B 21/002* (2013.01);
(Continued)

(58) Field of Classification Search
CPC ...... G01N 21/6458; G06T 2207/20224; G06T 3/4053; G02B 21/002; G02B 21/16; G02B 21/367; G02B 2207/113
See application file for complete search history.

(56) References Cited

U.S. PATENT DOCUMENTS

| 4,675,731 A | 6/1987 | Takasu et al. |
| 5,731,588 A | 3/1998 | Hell et al. |

(Continued)

FOREIGN PATENT DOCUMENTS

WO    WO 2011106323 A2 *  9/2011  ......... G01N 21/6458

OTHER PUBLICATIONS

Boruah et al., "Laser scanning confocal microscope with programmable amplitude, phase, and polarization of the illumination beam", Review of Scientific Instruments, 2009, vol. 80, 013705 pp. 1-8.

(Continued)

*Primary Examiner* — Bhavesh Mehta
*Assistant Examiner* — Ian Lemieux
(74) *Attorney, Agent, or Firm* — Hovey Williams LLP

(57) ABSTRACT

A method and a system for obtaining a high-resolution image of a volume of a sample using laser imaging are provided. The method includes a step of probing the volume of the sample with a first excitation beam having an intensity profile of maximum intensity at a center thereof, thereby obtaining a positive image of the volume. The method also includes a step of probing the volume of the sample with a second excitation beam having an intensity profile of minimum intensity at a center thereof and defining a peripheral region of maximum intensity around the center, thereby obtaining a negative image of the volume. The method finally includes a step of subtracting the negative image from the positive image, thereby obtaining the high-resolution image of the volume of the sample. Advantageously, embodiments of the invention can be probe- and fluorescence-independent, and be conveniently retrofitted into existing laser imaging systems.

26 Claims, 15 Drawing Sheets

(51) Int. Cl.
  *G02B 21/00* (2006.01)
  *G02B 21/16* (2006.01)
  *G02B 21/36* (2006.01)
  *G01N 21/64* (2006.01)

(52) U.S. Cl.
  CPC ............ *G02B 21/16* (2013.01); *G02B 21/367* (2013.01); *G02B 2207/113* (2013.01); *G06T 2207/20224* (2013.01)

(56) References Cited

U.S. PATENT DOCUMENTS

| | | | |
|---|---|---|---|
| 5,812,629 A * | 9/1998 | Clauser | A61B 6/032 378/37 |
| 5,866,911 A | 2/1999 | Baer | |
| 6,259,104 B1 * | 7/2001 | Baer | G02B 21/0056 250/458.1 |
| RE38,307 E | 11/2003 | Gustafsson et al. | |
| 7,485,875 B2 * | 2/2009 | Wolleschensky | G01N 21/6458 250/458.1 |
| 7,728,860 B2 | 6/2010 | Kawahara et al. | |
| 7,776,613 B2 | 8/2010 | Zhuang et al. | |
| 7,863,585 B2 | 1/2011 | Hell et al. | |
| 2002/0085293 A1 * | 7/2002 | Stuckey | G02B 21/06 359/831 |
| 2007/0115551 A1 * | 5/2007 | Spilman | G02B 27/286 359/489.07 |
| 2008/0018891 A1 * | 1/2008 | Hell | G01N 21/6458 356/317 |
| 2009/0046298 A1 * | 2/2009 | Betzig | G01N 21/6445 356/521 |
| 2009/0116707 A1 * | 5/2009 | Sutko | G06K 9/00134 382/128 |
| 2010/0059696 A1 * | 3/2010 | Heintzmann | G02B 21/0056 250/550 |
| 2010/0176307 A1 | 7/2010 | Hell et al. | |

OTHER PUBLICATIONS

Boruah, "Lateral resolution enhancement in confocal microscopy by vectorial aperture engineering", Applied Optics, 2010, vol. 49, No. 4, pp. 701-707.

Haeberlé et al., "Saturated structured confocal microscopy with theoretically unlimited resolution", Optics Communications, 2009, vol. 282, pp. 3657-3664.

Dorn et al., "Sharper focus for a radially polarized light beam", Physical Review Letters, 2003, vol. 91, No. 23, 233901.

Dehez et al., "Enhanced resolution in two-photon imaging using a TM01 laser beam at a dielectric interface", Optic Letters, 2009, vol. 34, No. 23, pp. 3601-3603.

Dehez et al., "Resolution and contrast enhancement in laser scanning microscopy using dark beam imaging" Optics Express, 2013, vol. 21, No. 13, pp. 15912-15925.

S. W. Hell et al., "Breaking the diffraction resolution limit by stimulated emission: stimulated emission depletion microscopy", Jun. 1, 1994, Optics Letters, vol. 19, No. 11, pp. 780-782, Optical Society of America.

S. Bretschneider et al., "Breaking the diffraction barrier in fluorescence microscopy by optical shelving", May 25, 2007, Physical Review Letters, vol. 98, pp. 218103-1-218103-4, The American Physical Society.

M. Hofmann et al., "Breaking the diffraction barrier in fluorescence microscopy at low light intensities by using reversibly photoswitchable proteins", Dec. 6, 2005, Proc. Natl. Acad. Sci. USA, vol. 102, pp. 17565-17569.

J. Bückers et al., "Simultaneous multi-lifetime multi-color STED imaging for colocalization analyses", Feb. 14, 2011, Optics Express, vol. 19, pp. 3130-3143.

J. B. Ding et al., "Supraresolution imaging in brain slices using stimulated-emission depletion two-photon laser scanning microscopy", Aug. 27, 2009, Neuron, vol. 63 (4), pp. 429-437.

H. Shroff et al., "Dual-color superresolution imaging of genetically expressed probes within individual adhesion complexes", Dec. 18, 2007, Proc. Natl. Acad. Sci. USA, vol. 104, No. 51. pp. 20308-20313.

M. Bates et al., "Multicolor super-resolution imaging with photoswitchable fluorescent probes", Sep. 21, 2007, Science, vol. 317, pp. 1749-1753.

B. Huang et al., "Three-dimensional super-resolution imaging by stochastic optical reconstruction microscopy", Feb. 8, 2008, Science, vol. 319, pp. 810-813.

P. Kner et al., "Super-resolution video microscopy of live cells by structured illumination", May 2009, Nature Methods, vol. 6 (5), pp. 339-342, Howard Hughes Medical Institute.

* cited by examiner

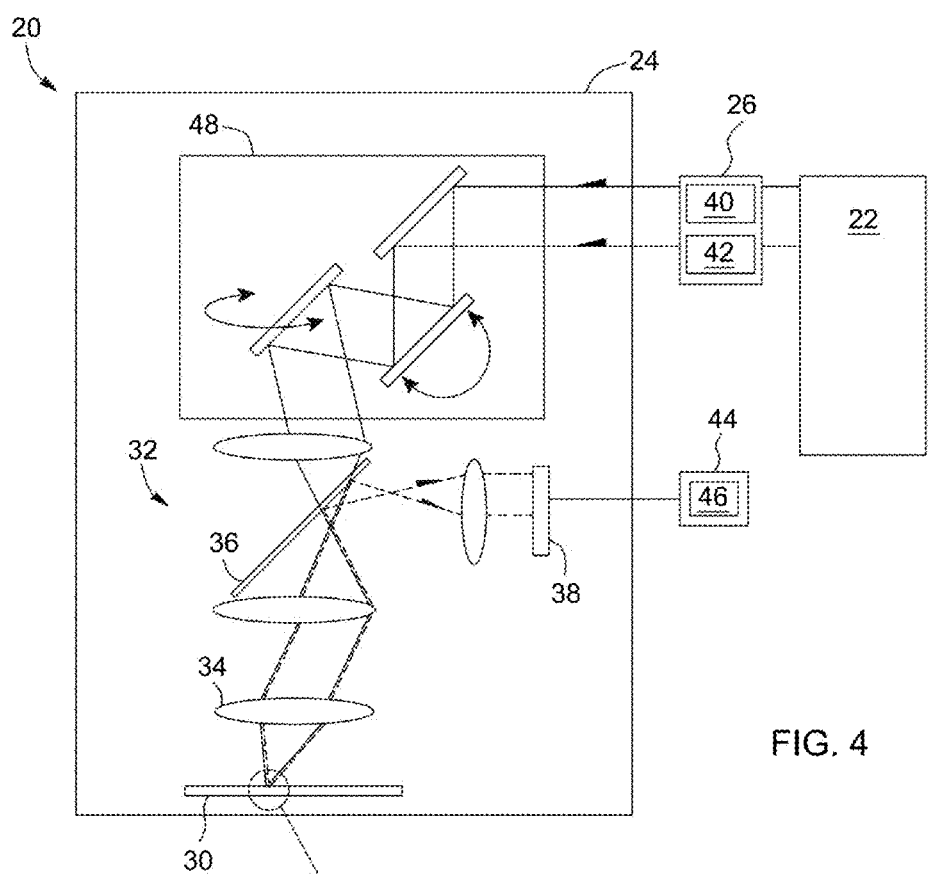
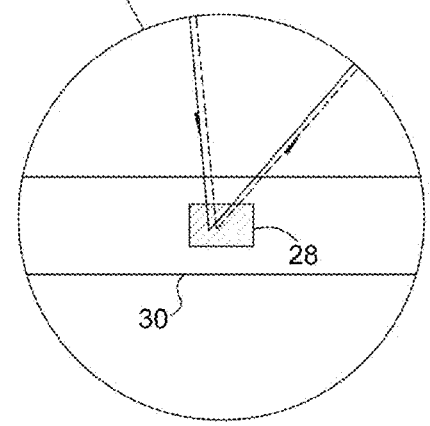
FIG. 4
FIG. 4A

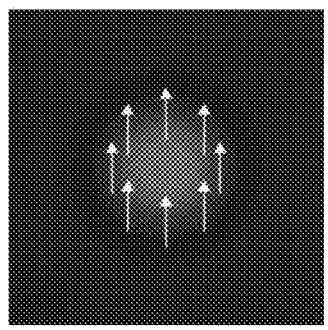 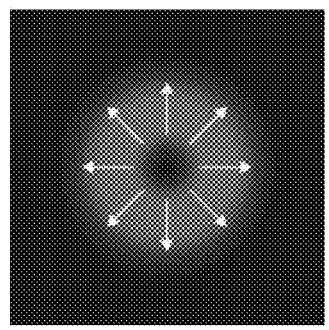 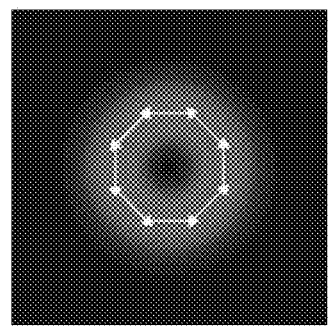
FIG. 15A  FIG. 15B  FIG. 15C
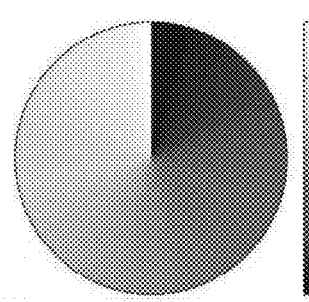 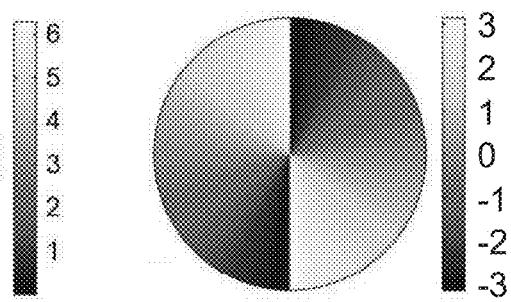
FIG. 16A  FIG. 16B

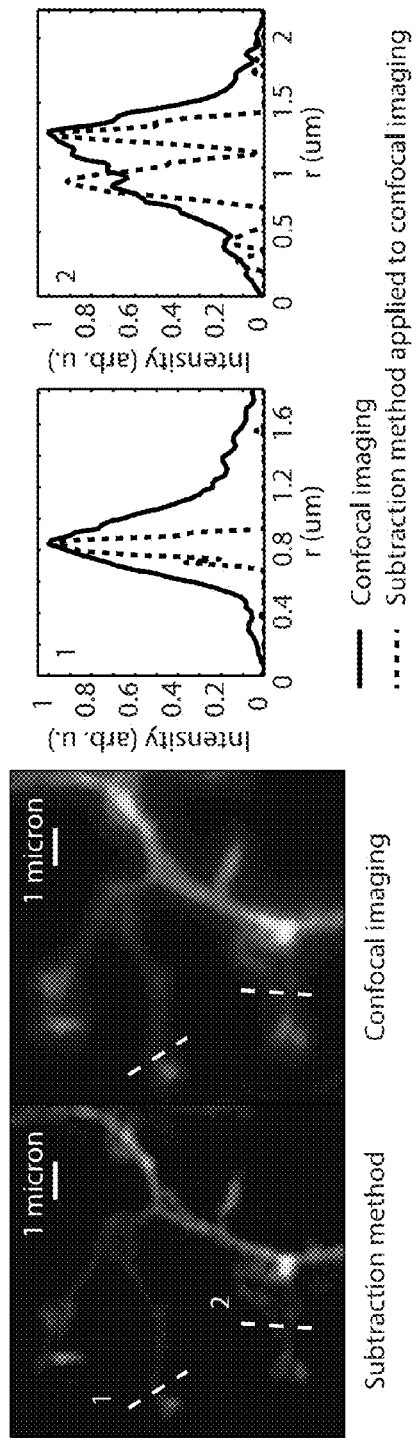
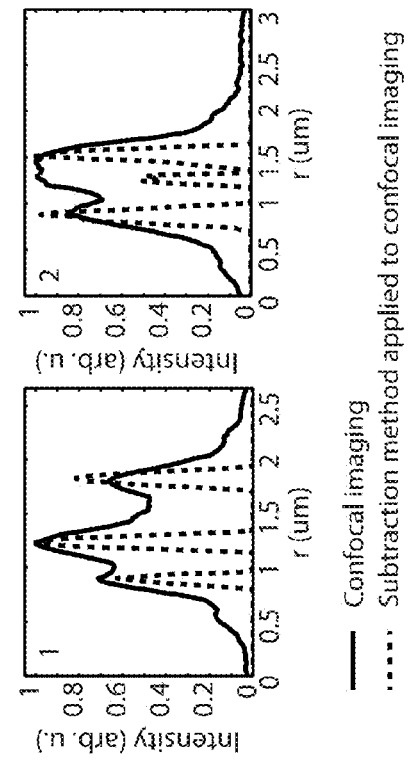
FIG. 18A
FIG. 18B

METHOD AND SYSTEM FOR IMPROVING RESOLUTION IN LASER IMAGING MICROSCOPY

FIELD OF THE INVENTION

The present invention relates to the field of laser imaging systems such as the type used in microscopy, and more particularly concerns a method and a system improving the image resolution of laser scanning microscopes.

BACKGROUND OF THE INVENTION

In laser scanning imaging systems, such as microscopes or macroscopes, an incident laser beam is focused on a specimen and the focal spot is scanned through the specimen. In conventional laser scanning imaging systems, the incident laser beam is focused by an objective lens to a diffraction-limited spot on or within the specimen, which may or may not be fluorescent. Scattered and reflected laser light as well as any re-emitted (i.e. fluorescent) light emanating from the illuminated spot is collected by the objective lens, and separated from the incident beam by one or more beam splitters. A photo-detector transforms this light signal emanating from the sample into an electrical signal which is recorded by a computer. The detected light originating from one illuminated diffraction-limited spot of the specimen represents one pixel in the resulting image. As the laser scans over the specimen, a whole image is obtained pixel by pixel, in which the brightness of each pixel corresponds to the relative intensity of detected light.

By way of example, FIG. 1 (PRIOR ART) shows an example of a laser scanning imaging system 20 used for two-photon excited fluorescence. The laser scanning imaging system 20 includes a laser module 22 for generating a laser beam and an imaging device 24 (i.e. laser scanning microscope) adapted to focus the laser beam into a diffraction-limited spot size within or on the surface of a sample 30, and to collect any light emanating from the sample 30 as a result of the probing by the laser beam. As known in the art, the laser scanning microscope generally includes imaging optics 32 such as an objective lens 34 and a beam splitter 36, an image sensor 38 sensing light emanating from the sample 30 upon being probed by the laser beam, as well as a scanning module 48 (e.g. a scan head) adapted to scan the laser beam over the sample 30.

Laser scanning microscopy methods (e.g. confocal, two-photon or multi-photon microscopy) are usually preferred to wide-field microscopy methods for their z-sectioning ability. For example, confocal and two-photon laser scanning fluorescence microscopes having better spatial resolution than conventional wide-field microscopes are now commonly employed for imaging narrow sections of biological structures, in which molecules of interest are tagged with fluorescent markers. Indeed, both confocal and two-photon laser microscopes can provide depths of field of the order of only a few microns, which leads to excellent optical sectioning capabilities. This key feature of laser scanning microscopy allows acquiring multiple in-focus images of thin sections at selected depths within a sample and therefore enables three-dimensional imaging of thick samples. However, the transverse resolution of laser scanning microscopy remains similar to that of wide-field microscopy.

Microscopy is generally limited in resolution by the diffraction barrier also known as the Abbe or Rayleigh limit. In theory, this limit is $\lambda/2$, where $\lambda$ is the optical wavelength of the light used to probe the material being investigated. In practice, however, this limit can only be reached with optimized high-numerical aperture instruments. For biomedical or material applications, high resolution is often needed and a large variety of methods have been developed to overcome this limit. Methods developed for enhancing the resolution of microscopes are often referred to as "super-resolution" or "hyper-resolution" methods.

Super-resolution methods can be classified into three categories. The first category relies on optical shaping of the excitation volume and includes the stimulated emission depletion (STED) microscopy developed by Stefan Hell. The STED approach is based on the depletion of fluorescence emission in a ring around the focal point using stimulated emission, triplet-state shelving, or reversible saturable optical fluorescence transitions (RESOLFT) [S. W. Hell et al., "Breaking the diffraction resolution limit by stimulated emission: stimulated emission depletion microscopy", *Opt. Lett.* vol. 19, pp. 780-782 (1994); S. W. Hell, "Process and device for optically measuring a point on a sample with high local resolution", U.S. Pat. No. 5,731,588 (1998); S. Bretschneider et al., "Breaking the diffraction barrier in fluorescence microscopy by optical shelving", *Phys. Rev. Lett.* vol. 98, pp. 218103 (2007); M. Hofmann et al., "Breaking the diffraction barrier in fluorescence microscopy at low light intensities by using reversibly photoswitchable proteins", *Proc. Natl. Acad. Sci. USA* vol. 102, pp. 17565-17569 (2005)]. A strong increase in resolution is obtained using this technique, but high peak power lasers, which can cause photobleaching and possibly photodamage, or specific probes (e.g. molecular absorbers/emitters) are needed. A STED macroscope would require the use of a high power laser to get enough intensity at the focus for the depletion, because the spot size is significantly larger in macroscopy compared to microscopy. Furthermore, STED cannot be retrofitted into an existing laser scanning microscope and is limited to fluorescence imaging. Complex multi-color confocal and single-color two-photon versions of STED exist, but they are more restrictive on the probe selection compared to conventional multi-color confocal and two-photon microscopes [J. Bückers et al., "Simultaneous multi-lifetime multi-color STED imaging for colocalization analyses", *Opt. Express* vol. 19, pp. 3130-3143 (2011); J. B. Ding et al., "Supraresolution imaging in brain slices using stimulated-emission depletion two-photon laser scanning microscopy", *Neuron* vol. 63, pp. 429-437 (2009)].

The second category relies on single molecule imaging and localization. It includes photo-activation localization microscopy (PALM), stochastic optical reconstruction microscopy (STORM), and many other methods based on active control of the emitting molecules using photo-activation or photo-switching [H. Shroff et al., "Dual-color superresolution imaging of genetically expressed probes within individual adhesion complexes", *Proc. Natl. Acad. Sci. USA* vol. 104, pp. 20308-20313 (2007); M. Bates et al., "Multicolor super-resolution imaging with photo-switchable fluorescent probes", *Science* vol. 317, pp. 1749-1753 (2007); B. Huang et al., "Three-dimensional super-resolution imaging by stochastic optical reconstruction microscopy", *Science* vol. 319, pp. 810-813 (2008); X. Zhuang et al., "Sub-diffraction image resolution and other imaging techniques" U.S. Pat. No. 7,776,613]. A high accuracy of molecule position is obtained using these methods, but specific probes and much longer acquisition times are needed. These methods are also subject to mathematical artifacts since they rely on calculations of the centroid of the diffraction spot. These methods are often applied to total internal reflectance fluorescence (TIRF) microscopy and oblique illumination microscopy, and their working distance is very limited.

The third category of super-resolution methods is referred to as "structured illumination" and allows improving the resolution of wide-field microscopes [P. Kner et al., "Super-resolution video microscopy of live cells by structured illumination", *Nature Methods* vol. 6, pp. 339-342 (2009)]. In brief, structured illumination consists in exciting fluorescent species in a sample using a beam made of periodic parallel lines produced by the interference between two laser beams. Multiple images of the sample are taken at different orientations and phases of the periodic pattern. Data acquisition is followed by sophisticated image processing in order to generate super-resolved images. A gain in resolution by a factor of two is obtained compared to conventional imaging systems, and resolution can be further enhanced if nonlinearity can be exploited.

Other approaches for enhancing resolution in laser scanning microscopy that have been proposed include works by B. R. Boruah [B. R. Boruah, "Lateral resolution enhancement in confocal microscopy by vectorial aperture engineering", *Applied Optics* vol. 49, pp. 701-707 (2010)] and O. Haeberlé and B. Simon [O. Haeberlé and B. Simon, "Saturated structured confocal microscopy with theoretically unlimited resolution", *Optics Communications* vol. 282, pp. 3657-3664 (2009)].

Commercial products based on STORM, on STED and on structured illumination have been put on the market. These instruments are specified for a resolution down to 20 nm (STORM), 50 nm (STED) and 100 nm (structured illumination). However, the cost of these systems is significantly higher than that of most current wide-field and laser scanning microscopes. Moreover, all of the above-mentioned super-resolution methods inherently rely on fluorescence and on specific photophysical properties of the fluorescent molecular probes.

There therefore remains a need for improving the resolution of laser scanning microscopic systems in a practical and cost effective manner.

SUMMARY OF THE INVENTION

According to an aspect of the invention, there is provided a method for obtaining a high-resolution image of a volume of a sample using laser imaging. The method includes the steps of:
(a) probing the volume of the sample with a first excitation beam having an intensity profile of maximum intensity at a center thereof, thereby obtaining a positive image of the volume;
(b) probing the volume of the sample with a second excitation beam having an intensity profile of minimum intensity at a center thereof and defining a peripheral region of maximum intensity around the center, thereby obtaining a negative image of the volume; and
(c) subtracting the negative image from the positive image, thereby obtaining the high-resolution image of the volume of the sample.

According to another aspect of the invention, there is provided a method for obtaining a combined image of a sample including a plurality of volumes using laser imaging. The method includes the steps of:
performing the method described above for obtaining a high-resolution image of a volume of a sample for each of the plurality of volumes of the sample, thereby obtaining a corresponding plurality of high-resolution images; and
combining the plurality of high-resolution images to form the combined high-resolution image of the sample.

According to another aspect of the invention, there is provided a laser imaging system for obtaining a high-resolution image of a volume of a sample. The laser imaging system includes:
a laser module for generating a laser beam;
an imaging device for imaging the volume of the sample;
a beam shaping module including:
    a mode converting assembly including a first output mode in which the laser beam is converted into a first excitation beam having an intensity profile of maximum intensity at a center thereof for obtaining, via the imaging device, a positive image of the volume of the sample, and a second output mode in which the laser beam is converted into a second excitation beam having an intensity profile of minimum intensity at a center thereof and defining a peripheral region of maximum intensity around the center for obtaining, via the imaging device, a negative image of the volume of the sample; and
    a switching device for switching between the first and second output modes of the mode converting assembly and outputting, one at a time, the first and second excitation beams for propagation within the imaging device to probe the volume of the sample; and
a processor for subtracting the negative image from the positive image, thereby obtaining the high-resolution image of the volume of the sample.

Advantageously, as will be readily understood by one of ordinary skill in the art, embodiments of the invention can be probe- and fluorescence-independent and as such do not rely upon the use of a specific dye with stringent absorption/emission requirements. Moreover, in biological sample imaging, the gain in resolution is not achieved at the expense of an increased laser power that would raise concerns about toxicity and tissue damage. In addition, extension to multicolor operation is straightforward.

Furthermore, according to some embodiments of the invention, existing laser scanning imaging systems can be retrofitted to include the beam shaping module as introduced above.

Other features and advantages of embodiments of the present invention will be better understood upon reading of preferred embodiments thereof with reference to the appended drawings.

BRIEF DESCRIPTION OF THE DRAWINGS

FIG. 4 is a schematic representation of a laser imaging system in accordance with an embodiment of the invention, wherein the imaging device is embodied by a two-photon excitation microscope. FIG. 4A in an enlargement of portion 4A of FIG. 4

FIGS. 7A to 7C were obtained using a 1.2 numerical aperture objective and a laser beam at a wavelength of 532 nm.

FIGS. 15A to 15C show the respective paraxial intensity profile and polarization orientation of a linearly polarized Gaussian beam (FIG. 15A), a radially polarized beam (FIG. 15B), and an azimuthally polarized beam (FIG. 15C).

FIGS. 16A and 16B show the phase of a laser beam transmitted by two first-order vortex plates.

FIGS. 18A and 18B show two experimental examples of resolution enhancement in confocal imaging obtained with an embodiment of the present invention. FIG. 18A compares conventional confocal images with high-resolution images of dendritic spines of cultured neurons transfected with m-Ruby. FIG. 18B makes the same comparison with neuronal growth cones, where details were revealed by immunohistochemical labeling of tubulin. It is to be noted that no deconvolution was used.

FIGS. 19A and 19B were obtained assuming a 1.2 numerical aperture objective and a laser beam at a wavelength of 532 nm.

DESCRIPTION OF PREFERRED EMBODIMENTS OF THE INVENTION

Figure 1:
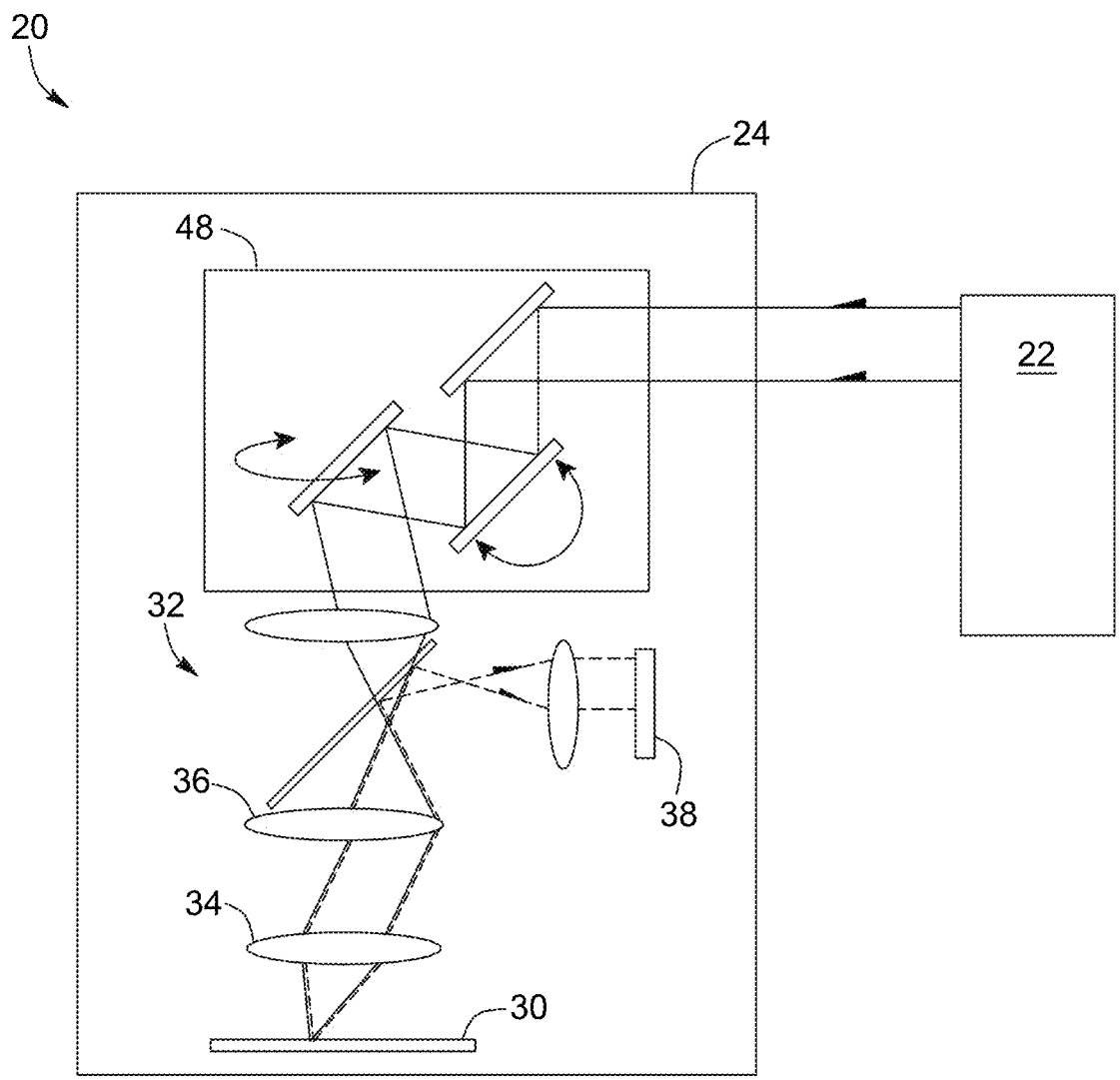
FIG. 1 (PRIOR ART) is a schematic representation of a conventional two-photon version of a laser scanning microscope.

The present invention generally relates to a method using laser imaging and a laser imaging system for obtaining a high-resolution image of a volume of a sample.

Method for Obtaining a High-Resolution Image of a Volume of a Sample

According to an aspect of the invention, there is provided a method for obtaining a high-resolution image of a volume of a sample using laser imaging.

Broadly speaking, the method involves probing the volume of the sample with a first excitation beam to obtain a positive image of the volume, probing this same volume of the sample with a second excitation beam to obtain a negative image of the volume, and subtracting the negative image from the positive image to obtain the high-resolution image of the volume of the sample. As will be described in further detail hereinbelow, it will be noted that the first and second excitation beams probe a volume of the sample that represents a same optical slice thickness and that corresponds to a focal point having the same spatial coordinates, thus ensuring that images representing the same structures are subtracted.

Throughout the present description, the term "resolution" relates to spatial resolution unless otherwise stated and is intended to refer to the capability of an imaging system to resolve closely placed objects or to distinguish fine details in a structure. Spatial resolution may be characterized by a point spread function (PSF), which describes the output of an imaging system to a point source or point object, and is expressed as length (e.g. as the full width at half maximum value of the PSF). As one of ordinary skill in the art will understand, the image to a point source has a defined size due to diffraction effects and, in practice, also to aberrations in the imaging optics forming the imaging system.

The term "high-resolution" generally refers to a resolution that equals or surpasses the resolution commonly achievable in conventional laser imaging methods and systems. More specifically, the term "high-resolution" refers to the image of the volume of a sample which is obtained by subtracting the negative image from the positive image of the volume. In addition, as mentioned above, the resolution of optical systems such as a microscope is generally limited physically by the diffraction barrier, also known as the Rayleigh limit or the Abbe limit. Embodiments of the invention provide high-resolution images that may allow circumventing this limit.

The term "laser imaging" broadly refers to the imaging techniques where laser radiation is used as the excitation source. Hence, it will be understood that the method according to embodiments of the invention may be applied to any imaging acquisition process whereby a laser beam is used to probe a volume of a sample, and light emanating from the volume of the sample as a result of this probing is collected and analyzed. The light emanating from the volume of the sample may originate from scattering or reflection of the laser beam, or may be re-emitted such as in the case of fluorescence or nonlinear optical processes. Examples of microscopic systems which may benefit from embodiments of the present invention include a confocal microscope, a one-photon or a multi-photon (e.g. two-photon) excitation microscope system, which may but need not involve fluorescence, a second-harmonic imaging or a third-harmonic imaging microscope, a reflectance microscope, a coherent anti-Stokes Raman scattering system, a stimulated Raman scattering system, a sum-frequency generation system, and the like.

It will further be understood that embodiments of the present invention could also be applied to optical macroscopy, in which the image size and the working distance of the optics are greater than in standard microscopy.

Furthermore, any appropriate sample including features of interest that could be observed using laser imaging may be probed using the method according to embodiments of the invention. In particular, the method could be used to improve fluorescence imaging of biological specimens.

Figure 2:
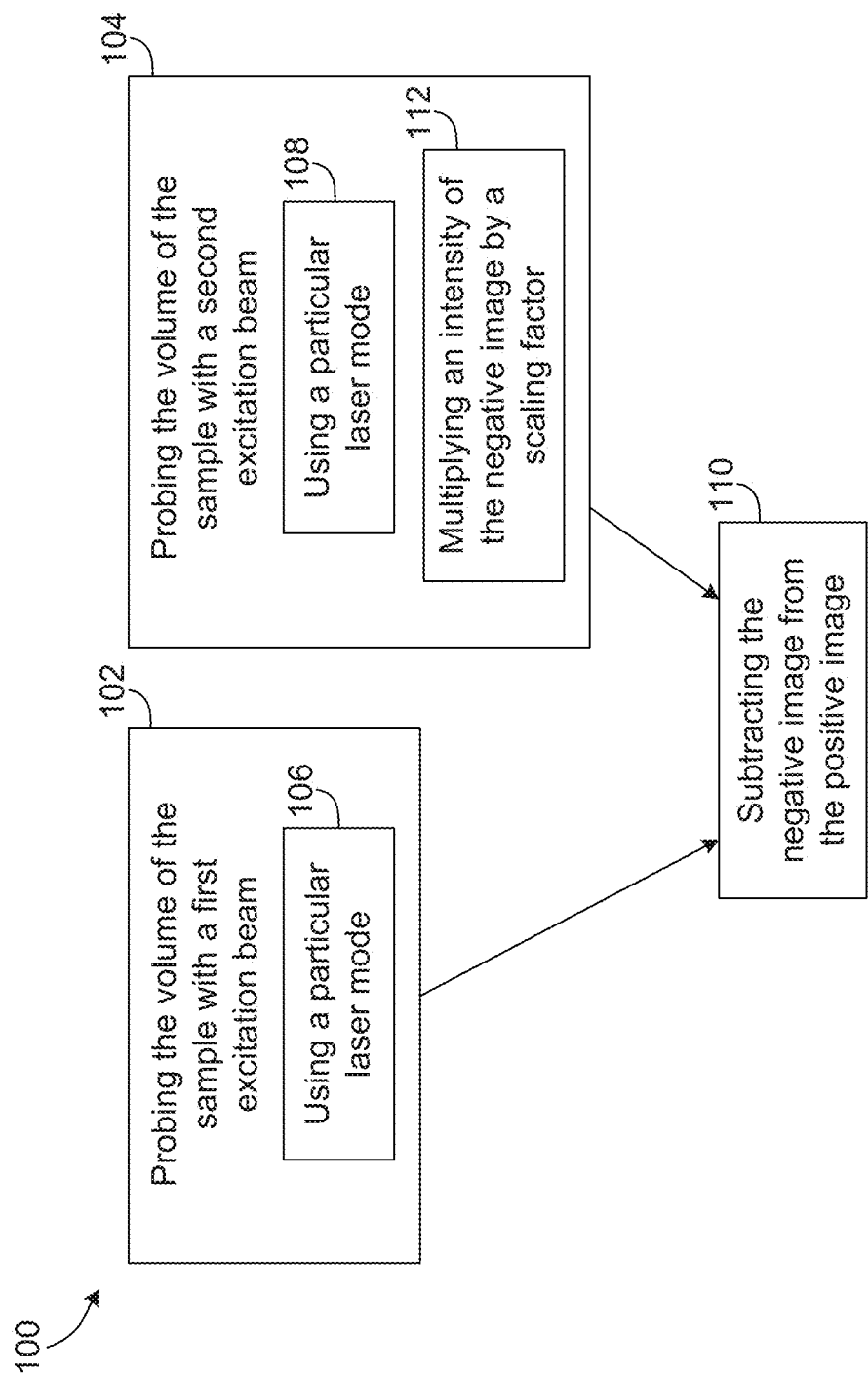
FIG. 2 is a flow chart of a method for obtaining a high-resolution image of a volume of a sample using laser imaging, in accordance with an embodiment of the invention.

Referring now to FIG. 2, there is shown a flow chart of an embodiment of the method 100, which can, by way of example, be performed with a laser imaging system such as that illustrated in FIGS. 3A to 3C and 4.

The method 100 includes a step 102 of probing the volume of the sample with a first excitation beam having an intensity profile of maximum intensity at a center thereof, thereby obtaining a positive image of the volume.

The method also includes a step 104 of probing the volume of the sample with a second excitation beam having an intensity profile of minimum intensity at a center thereof and defining a peripheral region of maximum intensity around the center, thereby obtaining a negative image of the volume.

The terms "first" and "second" as used herein in reference to excitation beams are solely employed for convenience are not intended to convey an order. In this regard, it will be appreciated that the steps 102 and 104 of probing the volume of the sample with the first and second excitation beams need not be performed in the exact order shown in FIG. 2. For example, in another embodiment, the step 104 of probing the volume of the sample with the second excitation beam may be performed before the step 102 of probing the volume of the sample with the first excitation beam. It is further to be noted that, for convenience, the first and second excitation beams will at times be referred to as the "positive" and "negative" beams, respectively, hence reflecting the fact that the first excitation beam is used to obtain the positive image and that the second excitation beam is used to obtain the negative image.

The term "intensity profile" as used herein generally refers to the spatial distribution of intensity of electromagnetic radiation of a beam as a function of lateral distance from the optical axis of the beam.

Still referring to FIG. 2, it will be understood by one of ordinary skill in the art that any appropriate laser mode having an intensity profile of maximum intensity at a center thereof may be used for probing the volume of the sample and obtain the positive image thereof. For example, in some embodiments, the step 102 of probing the volume of the sample with the first excitation beam may include using 106, as the first excitation beam, a linearly polarized Gaussian beam, a circularly polarized Gaussian beam or a radially polarized transverse magnetic (TM) beam. Preferably, it may be advantageous to use a circularly symmetric first excitation beam with a high signal-to-noise ratio since this yields higher signal-to-noise measurements and leads to a circularly symmetric PSF after processing.

Likewise, any appropriate type of "doughnut" laser mode having an intensity profile of minimum intensity at a center thereof and defining a peripheral region of maximum intensity around the center may be used for probing the volume of the sample and obtain the negative image thereof. For example, in some embodiments, the step 104 of probing the volume of the sample with the second excitation beam may include using 108, as the second excitation beam, a circularly polarized vortex beam, which is characterized by a spiral phase shift, or an azimuthally polarized transverse electric (TE) beam. As for the first excitation beam, it will be readily understood that the selection or use of one particular mode for the second excitation beam may depend on the intended application of the method 100. For example, in some embodiments, it may be advantageous to use a second excitation beam with circular symmetry, as it avoids distortions of the PSF after processing.

Figures 5A, 5B, 5C, 5D:
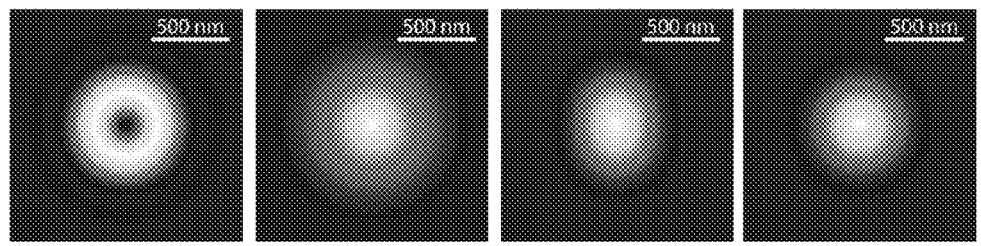
FIGS. 5A to 5D show the theoretical intensity distribution at the focus of a first-order azimuthally polarized mode (FIG. 5A), a first-order radially polarized mode (FIG. 5B), a linearly polarized Gaussian mode (FIG. 5C), and a circularly polarized Gaussian mode (FIG. 5D), using a 1.2 numerical aperture objective and a laser beam at a wavelength of 532 nm, in accordance with embodiments of the invention.

By way of example, FIGS. 5A to 5D show the theoretical intensity profile at the focus using a 1.2 numerical aperture objective of a first-order azimuthally polarized mode (FIG. 5A), which could be used as the second excitation beam, and a first-order radially polarized mode (FIG. 5B), a linearly polarized Gaussian mode (FIG. 5C), and a circularly polarized Gaussian mode (FIG. 5D), all three of which could be used as the first excitation beam. As will be readily recognized, each choice of mode may have advantages and drawbacks depending on the constraints of various applications. For example, when using high-numerical-aperture objective lenses, the focal spot of linearly polarized Gaussian beams is slightly elliptic (FIG. 5C), whereas when using low-numerical-aperture objectives, radially polarized laser beams have a zero of intensity at the center. On the other hand, circularly polarized Gaussian beams may be advantageous for their versatility and the absence of distortion of their PSF (FIG. 5D). At the focus, the beam size along the small axis of the spot of a linearly polarized Gaussian beam (FIG. 5C) is smaller than that of the corresponding circularly polarized Gaussian beam (FIG. 5D), resulting in an increase of resolution after processing. Besides, a strong complementarity between radially polarized and azimuthally polarized laser beams facilitates switching between those two types of mode. Therefore, in some applications, linearly polarized and radially polarized beams could also be preferred solutions.

It will be understood that, in embodiments of the invention, the fact that the positive and negative images are obtained by probing the same volume of the sample implies that the positive and negative images are obtained under the same imaging configuration. The expression "imaging configuration" is understood herein to refer to the setting of the probed volume of the sample, which is defined by the spatial coordinates of the focal point and the optical slice thickness. For example, if the positive and the negative images are obtained, in one embodiment, with a confocal laser scanning microscope, then the focal plane must be the same for the acquisition of both images, and the pinhole diameters used for the acquisition of both images must be chosen so that the positive and negative images have the same optical slice thickness. Alternatively, in other embodiments, the method may include obtaining the positive image with a confocal laser scanning microscope and the negative image with a two-photon laser scanning microscope, or vice versa, as long as the imaging configuration, that is the setting of the probed volume of the sample, remains the same for both images.

Referring back to FIG. 2, the method 100 further includes, once both the positive and negative images have been obtained, a step 110 of subtracting the negative image from the positive image, thereby obtaining the high-resolution image of the volume of the sample.

As mentioned above, the designation of "first" and "second" excitation beams is not meant to impose a particular order according to which the positive and negative images are to be obtained. Specifically, in some embodiments, the negative image of a particular volume may be acquired before the positive one without departing from the scope of the present invention.

As one of ordinary skill in the art will understand, the step 110 of subtracting the negative image from the positive image may be performed using any appropriate processor such as a computer, a microcontroller or any appropriate processing unit. The subtracting operation may be an intensity subtraction of the positive and negative images of the volume of the sample or any appropriate process known in the art. In other embodiments, rather than performing an intensity subtraction, an electric-field subtraction may be carried out in order to enhance the quality of the high-resolution image. This may be done by subtracting the square root of the intensity of the negative image from the square root of the intensity of the positive image for a linear process, and the $(2N)^{th}$ root for a nonlinear process of order N. This procedure may be generalized to any power of the signal intensity. Of course, any other subtracting scheme known in the art could alternatively be used, as well as any other comparable or equivalent operation scheme. As maxima of intensity of the positive and negative images may not be the same in some embodiments, the positive and negative images may be normalized prior to the subtracting operation in order to account for the difference in maximum intensity.

Figures 6A, 6B:
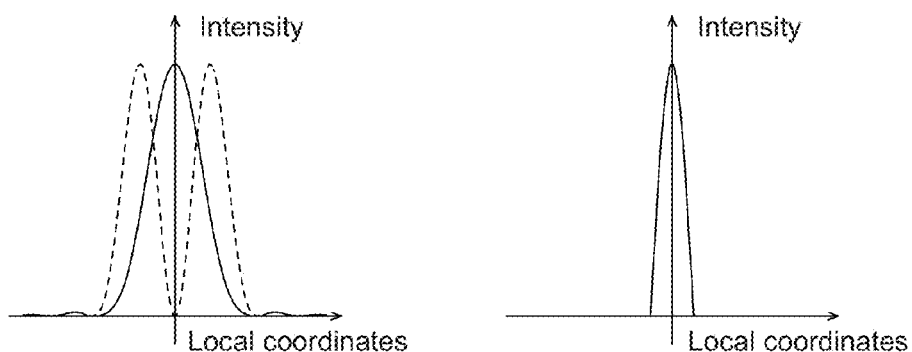
FIG. 6A is a graph of the intensity profile of the point spread function of the first (solid curve) and second (dashed curve) excitation beams that probe the volume of the sample in order to obtain the positive and negative images thereof, respectively.
FIG. 6B is a graph of the intensity profile of the high-resolution point spread function obtaining by subtracting the point spread function of the second excitation beam of FIG. 6A from the point spread function of the first excitation beam of FIG. 6A.

It will be recognized that the method 100 according to embodiments of the invention may help to reduce the size or the dimensions of the response of an imaging system to a point source or object (i.e. the PSF), for example the image of a single molecule. In laser microscopy, the shape of the PSF is directly related to the excitation volume. Hence, when an excitation laser beam having an intensity profile of maximum intensity at a center thereof (i.e. a "positive" beam) is used, the PSF presents a peak of intensity centered on the observed molecule. On the other hand, when an excitation laser beam having an intensity profile of minimum intensity at a center thereof and defining a peripheral region of maximum intensity around the center (i.e. a "negative" beam) is used, the PSF presents a ring of intensity centered on the observed molecule. In this regard, FIG. 6A is a graph of the intensity profile of the PSF of the first (solid curve) and second (dashed curve) excitation beams, which are used to probe the volume of the sample in order to obtain the positive and negative images thereof, respectively.

Referring back to FIG. 2, by performing the step 110 of subtracting the negative image from the positive image, a narrower PSF is obtained, and the resolution of the microscope is consequently increased. This is exemplified in FIG. 6B, which illustrates the intensity profile of the high-resolution PSF resulting from the subtraction of the PSF of the second excitation beam of FIG. 6A (dashed curve) from the PSF of the first excitation beam of FIG. 6A (solid curve). It will be apparent to those of ordinary skill in the art that the smaller the diameter of the hole of the PSF of the second excitation beam, the better the resolution of the resulting high-resolution image.

One of ordinary skill in the art will also understand that the same reasoning remains valid for complex structures since any image may be interpreted as the convolution between the object and the PSF. Hence, by subtracting the negative image from the positive image, an increase of resolution and contrast can be obtained.

When structures larger than the PSF of the second excitation beam are imaged, structure edges are detected with higher position accuracy using the subtraction method, but the inner part of the structure is darkened due to the subtraction. This effect can be compensated for by using image information contained in the intensity profile of the positive image.

Figure 19A:
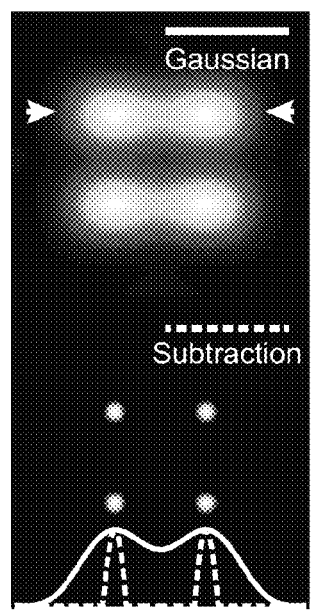
FIGS. 19A and 19B show two theoretical demonstrations of resolution enhancement in confocal imaging obtained with an embodiment of the present invention.
Figure 19B:
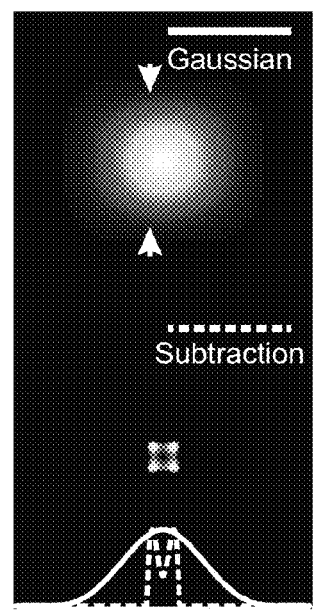

Referring now to FIGS. 19A and 19B, there is shown a theoretical demonstration of resolution enhancement using the method according an embodiment of the invention. FIGS. 19A and 19B were obtained assuming a 1.2 numerical aperture objective and a laser beam at a wavelength of 532 nm. The scale bar is 500 nanometers In each of FIGS. 19A and 19B, the top portion shows theoretical images of four point sources using confocal microscopy with a linearly polarized Gaussian beam. The middle portion shows theoretical images of the same four point sources using the subtraction method according to an embodiment of the invention with a circularly polarized Gaussian beam for the first excitation beam and an azimuthally polarized beam for the second excitation beam. Finally, the bottom portion shows the intensity profile of the images obtained with the linearly polarized Gaussian beam (solid curve) and using the subtraction method (dashed curve).

In FIG. 19A, the four point sources are separated from one another by the limit of resolution of confocal microscopy using a linearly polarized Gaussian beam, while in FIG. 19B, the four point sources are separated from one another by a distance about two times smaller than the limit of resolution of confocal microscopy using a linearly polarized Gaussian beam. As can be seen, in FIG. 19B, the point sources cannot be resolved using conventional confocal microscopy but are well resolved using the subtraction method according to an embodiment of the invention. The resolution limit is defined herein as a 75% contrast between the peaks and the valley between those peaks.

Referring back to FIG. 2, some embodiments of the method 100 may include, prior to the step 110 of subtracting the negative image from the positive image, a step 112 of multiplying an intensity of at least one of the positive and negative images by a scaling factor, in order to enhance a contrast of the high-resolution image. For example, the case where the intensity of the negative image is multiplied by a scaling factor may be expressed mathematically as follows:

$$PSF_{(HR)} = PSF_{(+)} - g \cdot PSF_{(-)},$$

where $PSF_{(HR)}$, $PSF_{(+)}$ and $PSF_{(-)}$ are respectively the high-resolution, positive and negative PSFs, and g is the scaling factor. As will be understood by one of ordinary skill in the art, when the value of g is increased, negative values of $PSF_{(HR)}$ that are generated beyond the edges of the peak of $PSF_{(+)}$ are set to zero because they have no physical meaning.

It will also be recognized that performing the step 112 of multiplying by a scaling factor may be advantageous because it yields a physical contrast enhancement without compromising detection sensitivity. Such contrast enhancement has the advantage that is depends neither on a priori information about the structure being imaged nor on characteristics of the excitation and/or detection system, as opposed to deconvolution approaches known in the art.

In some embodiments, the method 100 may be used to obtain high-resolution images of fluorescent molecules having a nonzero excitation lifetime. Due to this characteristic, fluorescent molecules become saturated above specific excitation intensity and the hole at the center of the negative beam becomes smaller. An optical saturation of the excitation can also be done in some embodiments to improve the resolution.

Figures 7A, 7B, 7C:
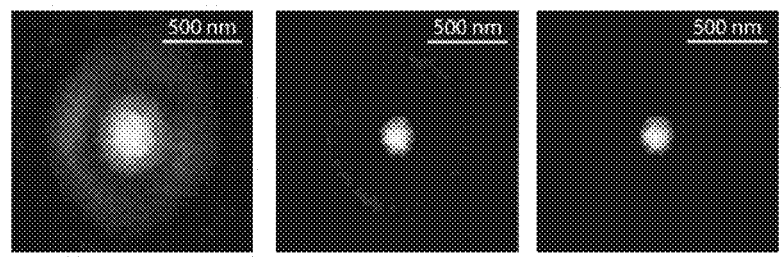
FIGS. 7A to 7C show the experimentally obtained point spread function of a linearly polarized Gaussian beam without processing (FIG. 7A), after processing through image subtraction and contrast enhancement (FIG. 7), and after Gaussian beam defocusing and the same processing as in FIG. 7B (FIG. 7C).

Moreover, experimental PSFs generally exhibit strong side lobes when the back aperture of the objective lens of the laser imaging system is overfilled. Overfilling the objective lens is usually done to fully exploit the numerical aperture of the objective lens and, thus, get a resolution closer to the diffraction limit. In some embodiments of the present invention, the intensity of side lobes is strongly reduced after processing, as shown in FIGS. 7A and 7B, where the experimentally obtained PSF of a linearly polarized Gaussian beam using a 1.2 numerical aperture objective and a laser beam at a wavelength of 532 nm is shown without (FIG. 7A) and after processing (FIG. 7B). Furthermore, as resolution improvement in the method according to embodiments of the invention can be strongly determined by the hole diameter of the intensity profile of the "negative" beam, a slight defocus may be applied to the "positive" beam in order to suppress side lobes with minimal effect on the resolution improvement after processing (FIG. 7C). Advantageously, one may also change the collimation of the "positive" beam, or reduce its size at the back aperture of the objective lens.

In some embodiments, different excitation wavelengths for the first and second excitation beams may be used, thus enabling multi-color applications of the method.

Figure 8:
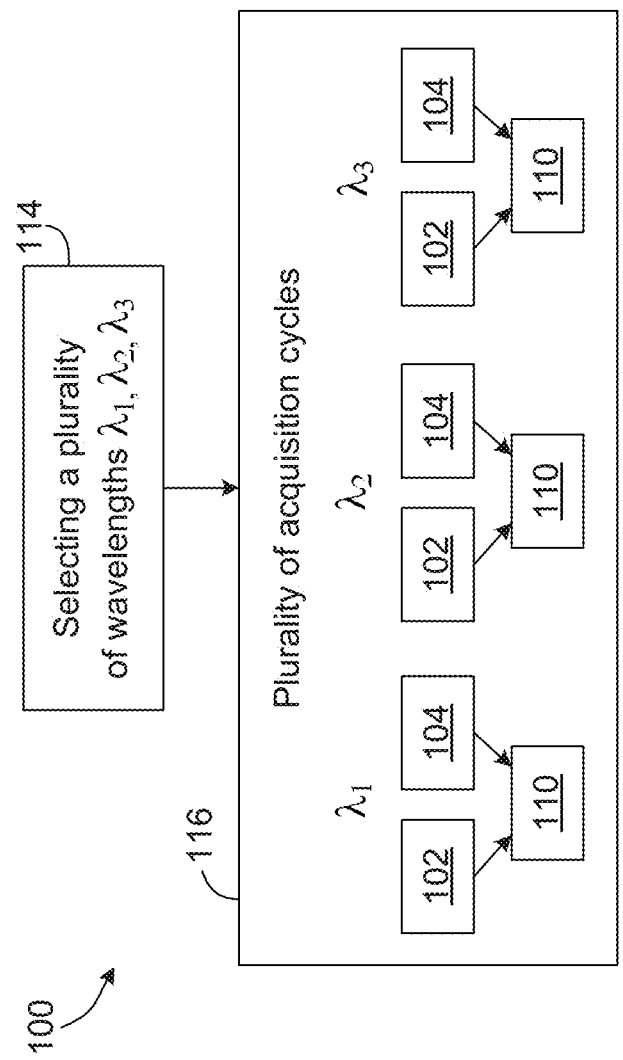
FIG. 8 is a flow chart of a method for obtaining a high-resolution image of a volume of a sample using laser imaging, in accordance with an embodiment of the invention, wherein the method is performed at a plurality of excitation wavelengths.

In this regard, FIG. 8 shows a flow chart of an embodiment of the method 100, wherein the method 100 is performed at a plurality of excitation wavelengths. This embodiment includes a step 114 of selecting a plurality of excitation wavelengths at which the volume of the sample may be probed. The method 100 according to this embodiment further includes performing 116 the steps 102 and 104 of probing the volume of the sample with the first and second excitation beams for obtaining the positive and negative images thereof and the step 110 of subtracting the negative image from the positive image for a plurality of acquisitions cycles, the first and second excitation beams having a different one of the plurality of excitation wavelengths for each of the acquisition cycles. For example, in FIG. 8, three such acquisition cycles are performed at wavelengths $\lambda_1$, $\lambda_2$ and $\lambda_3$. It will be understood that depending on the intended application, the plurality of acquisition cycles may be performed sequentially (sequential multi-color applications) or simultaneously (simultaneous multi-color applications), without departing from the scope of the invention.

The method according to embodiments of the invention may also be applied to two or multi-beam imaging modalities such as a coherent anti-Stokes Raman scattering (CARS) system, a stimulated Raman scattering system and a sum-frequency generation system. In particular, as known in the art, in CARS microscopy two tightly synchronized laser beams of different wavelengths (e.g. a pump laser beam and a Stokes laser beam) are directed coaxially onto a sample, wherein the difference in frequency between the two laser beams matches a molecular vibrational transition within the sample. In order to generate a signal, the two laser beams must be overlapped in both space and time at the volume of the sample being probed.

Figure 9:
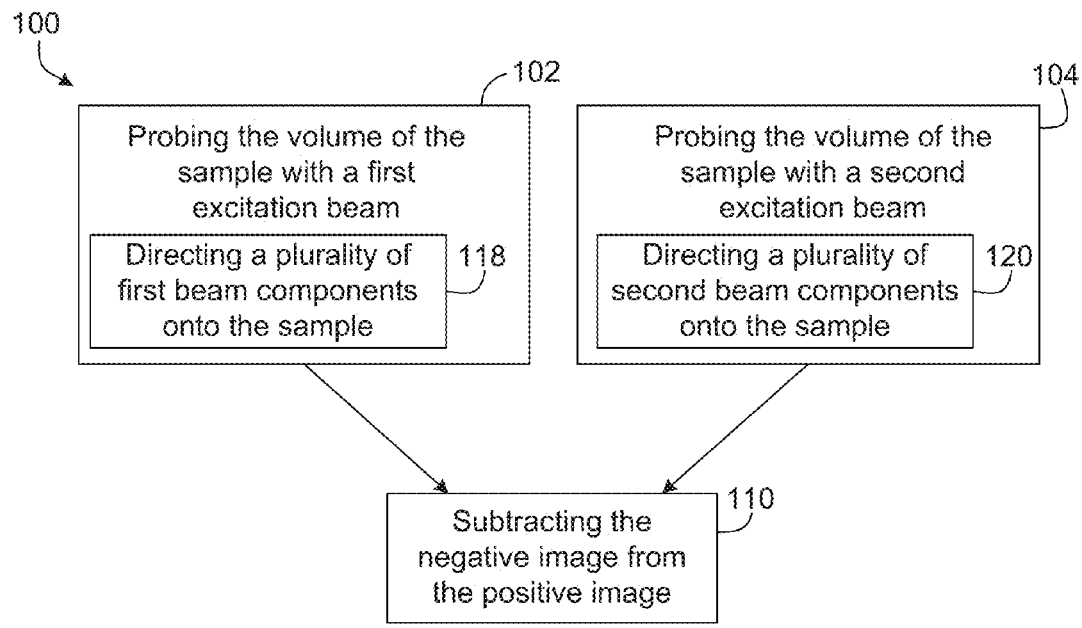
FIG. 9 is a flow chart of a method for obtaining a high-resolution image of a volume of a sample using laser imaging, in accordance with an embodiment of the invention, wherein the method involves multi-beam laser imaging.

Referring to FIG. 9, there is shown a flow chart of an embodiment of the method 100, wherein the method 100 is applied to obtain a high-resolution image of a volume of a sample using laser imaging, the method 100 involving multi-beam laser imaging.

In the illustrated embodiment, the step 102 of probing the volume of the sample with the first excitation beam includes directing 118 a plurality of first excitation beam components onto the sample in a manner such that the plurality of first excitation beam components spatially and temporally overlap with one another to form the first excitation beam at the volume of the sample.

Likewise, the step 104 of probing the volume of the sample with the second excitation beam includes directing 120 a plurality of second excitation beam components onto the sample in a manner such that the plurality of second excitation beam components spatially and temporally overlap with one another to form the second excitation beam at the volume of the sample. It will be understood herein that because the zone of interaction between the plurality of second excitation beam components is their overlap region, only one of the second excitation beam components needs to be "negative", that is, to have an intensity profile of minimum intensity at a center thereof and to define a peripheral region of maximum intensity around the center. Alternatively, if a higher "negative" signal is required, more than one of the second excitation beam components may be selected as "negative" beams.

As one of ordinary skill in the art will readily understand, laser imaging systems or microscopes usually involve a scanning of the laser beam over the sample in order to build an image thereof on a pixel-by-pixel basis, each pixel representing the observation of one volume. The method described above and illustrated in the flow charts of FIGS. 2, 8 and 9 may therefore be applied for each pixel of the image to be constructed, resulting in a full image of the sample when these pixels are combined as is well known to those of ordinary skill in the art.

Figure 10:
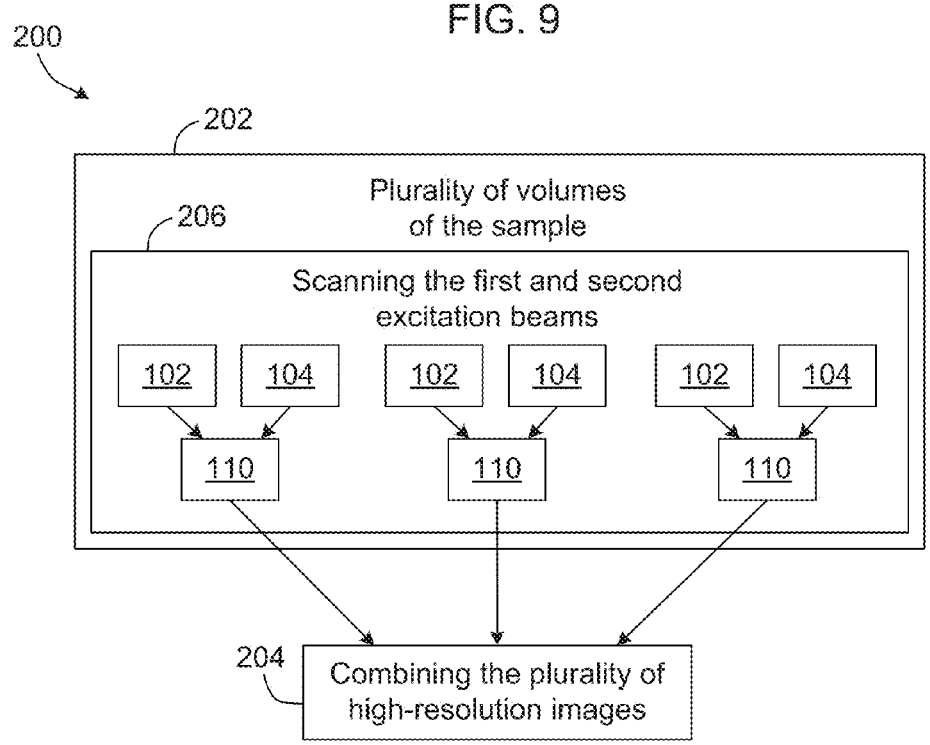
FIG. 10 is a flow chart of a method for obtaining a combined image of a sample including a plurality of volumes using laser imaging, in accordance with an embodiment of the invention.

In this regard, referring now to FIG. 10, there is shown a flow chart of an embodiment of a method 200 for obtaining a combined high-resolution image of a sample including a plurality of volumes.

The method 200 includes a step 202 of performing for each of the plurality of volumes of the sample the method 100 described above and exemplified in FIGS. 2, 8 and 9, thereby obtaining a corresponding plurality of high-resolution images. The method 200 also includes a step 204 of combining the plurality of high-resolution images to form the combined high-resolution image of the sample. The position of each pixel in the combined high-resolution image of the sample may be given by the center of the excitation laser beam when the pixel is recorded. With the spatial coordinates of each pixel associated with each of the plurality of volumes of the sample being given by the scanning parameter of the scan head, the combination of the plurality of high-resolution images is made pixel by pixel, and a combined high-resolution image is obtained. Equivalently, multiple images may be taken from a large sample by moving the sample between acquisitions of consecutive images; a precise knowledge of the number of pixels corresponding to the sample displacement allows reconstructing a combined high-resolution image of the full sample. Preferably, the step 202 of performing the method 100 for each volume of the sample includes scanning 206 the first and second excitation beams over the plurality of volumes of the sample.

One of ordinary skill in the art will readily understand that the probing of each of the plurality of the volumes of the sample with the first and second excitation beams, and the subsequent processing (e.g. subtracting) of the acquired data need not be done consecutively or separately for each pixel. For example, data may be obtained for the positive image of a series of pixels with the first excitation beam before switching to the second excitation beam for another pass on the same volumes of the sample. Moreover, subtracting the negative image from the positive for each of the plurality of volumes of the sample may be done concurrently to the scanning 206 of the first and second excitation beams over the sample or once all data has been obtained.

Laser Imaging System

According to another aspect of the invention, there is provided a laser imaging system for obtaining a high-resolution image of a volume of a sample.

Figure 3A:
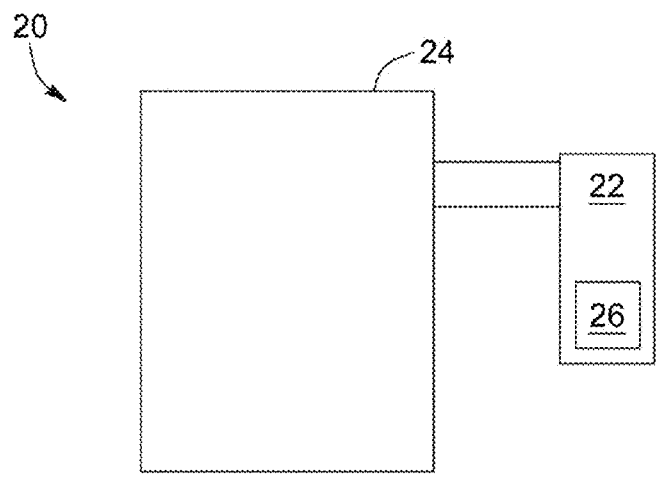
FIGS. 3A to 3C are schematic representations of a laser imaging system, in accordance with embodiments of the invention.
Figure 3B:
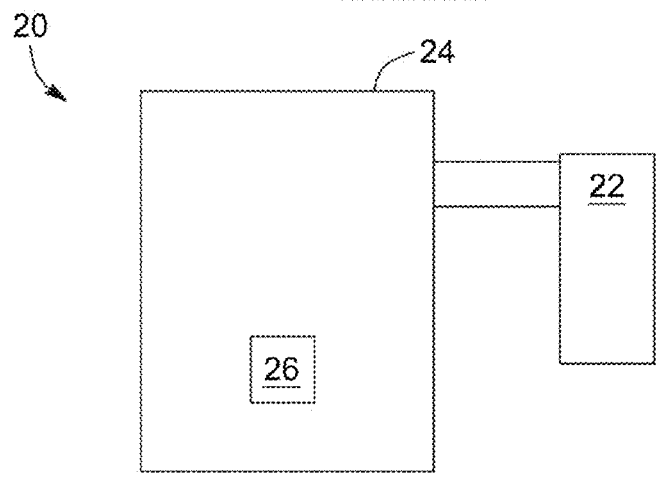
Figure 3C:
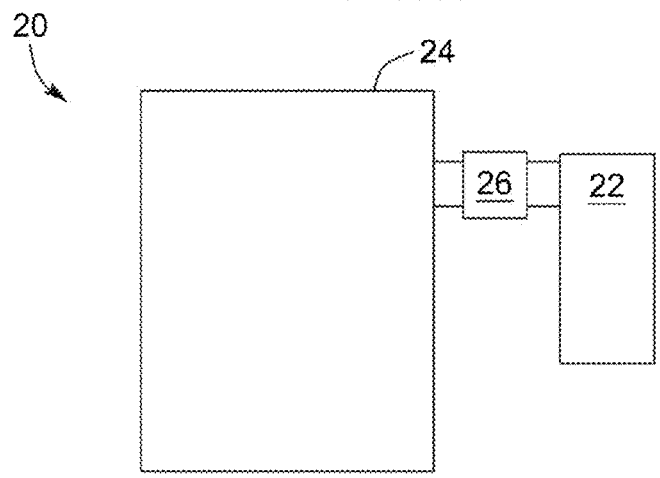

Referring to FIGS. 3A to 3C, a laser imaging system 20 according to one embodiment is shown. Broadly speaking, the laser imaging system 20 includes a laser module 22 and an imaging device 24, which may be optically linked to each other through optical fibers (not shown) or free space propagation. According to embodiments of the present invention, the laser imaging system 20 also includes a beam shaping module 26, which may, depending on the intended applications, be integrated into either the laser module 22 (FIG. 3A) or the imaging device 24 (FIG. 3B), or be separated from and disposed between the laser module 22 and the imaging device 24 (FIG. 3C). The beam shaping module 26 enables the probing of the volume 28 of the sample 30 mounted on the imaging device 24 with a first and a second excitation beam, as will be further explained below.

The laser module 22 may be embodied by any appropriate device or combination of devices apt to generate a laser beam which can be used to probe the volume 28 of sample 30 in the context of the present system 20. As used herein the "laser beam" is understood to refer to a spatially-coherent beam of electromagnetic radiation, nearly monochromatic or having a predetermined spectral profile. The electromagnetic radiation may be photons of energy encompassing the visible, infrared and ultraviolet portions of the electromagnetic spectrum. In embodiments of the present invention, the laser module 22 may be a gas laser, a diode-pumped solid-state laser, a laser diode, a fiber laser, a mode-locked Ti:sapphire laser, a supercontinuum laser source, an optical parametric oscillator (OPO), or the like.

The laser imaging system according to embodiments may be applied to various laser imaging modalities. Examples of laser imaging systems which could benefit from embodiments of the present invention include a confocal microscope, a one-photon or multi-photon (e.g. two-photon) microscope system, which may but need not involve fluorescence, a second-harmonic imaging or a third-harmonic imaging microscope, a reflectance microscope, a coherent anti-Stokes Raman scattering system, a stimulated Raman scattering system, a sum-frequency generation system, and the like.

Referring now to FIG. 4, there is shown an embodiment of the laser imaging system 20 in which the imaging device 24 is a microscope of the type used for two-photon excitation fluorescence measurements. The imaging device 24 includes imaging optics 32, which may include an objective lens 34 and a beam splitter 36. The imaging optics 32 is configured to receive either one of the first and second excitation beams from the beam shaping module 26 and to focus the same onto the volume 28 of the sample 30. The imaging device 24 also includes an image sensor 38 (e.g. a photo-detector) sensing electromagnetic radiation emanating from the volume 28 of the sample 30 upon being probed by the first and second excitation beams and producing therefrom the positive and negative images of the volume 28, respectively.

The objective lens 34 focuses the laser beam onto a diffraction-limited spot size within or on the surface of the sample 30 (see FIG. 4A). Light from the illuminated spot is then re-collected by the objective lens 34 and separated by the beam splitter 36. In the two-photon excitation microscopy example the collected light corresponds to fluorescence from the sample, although in other embodiments it may represent scattered, reflected or otherwise re-emitted light. The light signal coming from the illuminated spot and within the optical slice is detected by the image sensor 38 and transformed into an electrical signal. This electrical signal may then be integrated in a pixel centered on the position of the focal spot. Of course, one of ordinary skill in the art will readily understand that this configuration is shown by way of example only and that the imaging device 24 can, in practice, be embodied by a number of other components and configurations. More particularly, in other embodiments, the imaging device 24 may be a confocal microscope, or any other type of laser scanning microscopes or imaging systems including those based on linear or nonlinear optical generation processes.

The beam shaping module 26 acts on the laser beam generated by the laser module 22 in order to provide, at different moments in time, either a "positive" or a "negative" excitation beam. In some embodiments, the beam shaping module 26 can be retrofitted into an existing laser imaging system 20. Alternatively, laser systems 20 may be built with the beam shaping module 26 already incorporated therein. It will additionally be understood, as mentioned above, that the beam shaping module 26 may be a separate component inserted between the laser module 22 and imaging device 24 (FIG. 3C) or be integrated into either one of these modules (FIGS. 3A and 3B).

The beam shaping module 26 generally includes a mode converting assembly 40 and a switching device 42. The mode converting assembly 40 has a first output mode in which the laser beam is converted into the first excitation beam having an intensity profile of maximum intensity at a center thereof for obtaining, via the imaging device 24, the positive image of the volume 28 of the sample 30. The mode converting assembly 40 also includes a second output mode in which the laser beam is converted into the second excitation beam having an intensity profile of minimum (e.g. null) intensity at a center thereof and defining a peripheral region of maximum intensity around the center for obtaining, via the imaging device 24, the negative image of the volume 28 of the sample 30.

The switching device 42 allows for switching between the first and second output modes of the mode converting assembly 40 and for outputting, one at a time, the first and second excitation beams for propagation within the imaging device 24 to probe the volume 28 of the sample 30. Preferably, the switching device 42 of the beam shaping module 26 permits to switch rapidly between the two beam profiles.

The laser imaging system 20 further includes a processor 44 for subtracting the negative image from the positive image, thereby obtaining the high-resolution image of the volume 28 of the sample 30. In the illustrated embodiment, the processor 44 is coupled to the image sensor 38 of the imaging device 24 and configured to receive therefrom data corresponding to the positive and the negative images, for example as electrical signals. The processor 44 then subtracts the data corresponding to the negative image from the data corresponding to the positive image to yield the high-resolution image. The processor 44 may be a computer, a microcontroller, or any other type of appropriate processing unit.

Optionally, in some embodiments, the processor 44 may include a contrast-enhancing module 46 multiplying the intensity of at least one of the positive and negative images by a scaling factor prior to subtracting the negative image from the positive image. As described above, in the particular case where the negative image is multiplied by a scaling factor, the effect of the contrast-enhancing module 46 on the high-resolution image of the volume of the sample may be described by the equation $PSF_{(HR)} = PSF_{(+)} - g \cdot PSF_{(-)}$, where g is the scaling factor. In other embodiments, the contrast-enhancing module 46 may be provided as a separate processing device.

As mentioned above, laser imaging systems or microscopes usually involves a scanning of the laser beam over the sample in order to build an image thereof pixel by pixel, each pixel representing the observation of one volume. In this regard, in some embodiments, the imaging device 24 of laser imaging system 20 may preferably include a scanning module 48 (e.g. a scan head) for scanning the first and second excitation beams over a plurality of volumes 28 of the sample 30 so as to obtain a corresponding plurality of pairs of positive and negative images (e.g. pixels). In such embodiments, the processor 44 is further adapted to subtract the negative image of each of the pairs from the respective positive image, thereby obtaining the high-resolution image (e.g. pixel) for each of the volumes 28 of the sample 30.

As discussed above, embodiments of the present invention may be used for multi-color applications so that a high-resolution image of a volume of a sample may be obtained at different excitation wavelengths. Depending on the intended applications, sequential or simultaneous multi-color applications may be achieved.

In the case of sequential multi-color applications, the laser module may include a wavelength-adjusting mechanism for adjusting a wavelength of the laser beam. The wavelength-adjusting mechanism may be embodied by a laser with tunable filters, an optical parametric oscillator, and the like. Alternatively, the laser module may include a plurality of laser sources operable to emit a corresponding plurality of beam components, each at a different wavelength, wherein one of the beam components is used to generate the laser beam. Furthermore, the laser source may also include a spectrally broad laser source such a supercontinuum laser source or an amplified spontaneous emission (ASE) source provided with a tunable spectral filter such as dielectric bandpass filters, a set of prism with a slit, acousto-optical tunable filters, and the like.

In the case of simultaneous multi-color applications, the laser module may include a spectrally broad laser source (e.g. a supercontinuum laser source or an ASE source) or a plurality of laser sources operable to emit, each at a different wavelength, a corresponding plurality of beam components. The plurality of beam components may then be combined and outputted by the laser module as the laser beam. This laser beam may then be received by the beam shaping module and be converted into the first and second excitation beams. In such embodiments, the first and second excitation beams are thus respectively composed of a plurality of first and second excitation beam components, each at different wavelength. The plurality of first and second excitation beam components may be used to obtain, via the image device, a corresponding plurality of pairs of positive and negative images. Finally, the processor may be adapted to subtract the negative image of each of the pairs from the respective positive image, so as to obtain a high-resolution image of the volume of the sample at each of the plurality of wavelengths of the plurality of laser sources.

Some embodiments of the laser imaging system may also be applied to two or multi-beam imaging modalities such as CARS systems, stimulated Raman scattering systems and sum-frequency generation systems.

In embodiments where the laser imaging system is adapted for CARS microscopy, the laser module preferably includes two laser sources capable of producing two tightly synchronized laser beam components having different wavelengths (e.g. a pump laser beam and a Stokes laser beam). This pair of correlated laser beam components exits the laser module as the laser beam, which is received by the beam shaping module for conversion thereof into the first and second excitation beams. The first and second excitation beams are then directed, one at a time and via the imaging device, onto a volume of a sample.

More specifically, the first excitation beam is made of a pair of first excitation beam components which are directed onto the sample in a manner such that the two first excitation beam components spatially and temporally overlap with one another to form the first excitation beam at the volume of the sample. Likewise, the second excitation beam is made of a pair of second excitation beam components which are directed onto the sample in a manner such that the two second excitation beam components spatially and temporally overlap with one another to form the second excitation beam at the volume of the sample. As mentioned above, it will be understood herein that because the zone of interaction between the two second excitation beam components corresponds to their overlap region, only one of the two second excitation beam components need to be "negative". However, if a higher "negative" signal is required, the two second excitation beam components of the second excitation beam may be selected as "negative" beams.

Exemplary Embodiments of the Beam Shaping Module

Referring now to FIGS. 11 to 14, exemplary embodiments of the beam shaping module 26 are shown by way of examples. As mentioned above, the beam shaping module 26 receives the laser beam 50 from the laser module and generally includes a mode converting assembly 40 to create the "positive" first and "negative" second excitation beams 52a and 52b in the first and second output modes thereof, respectively, and a switching device 42 to switch between these two beams 52a and 52b, preferably at high speed.

Figure 11:
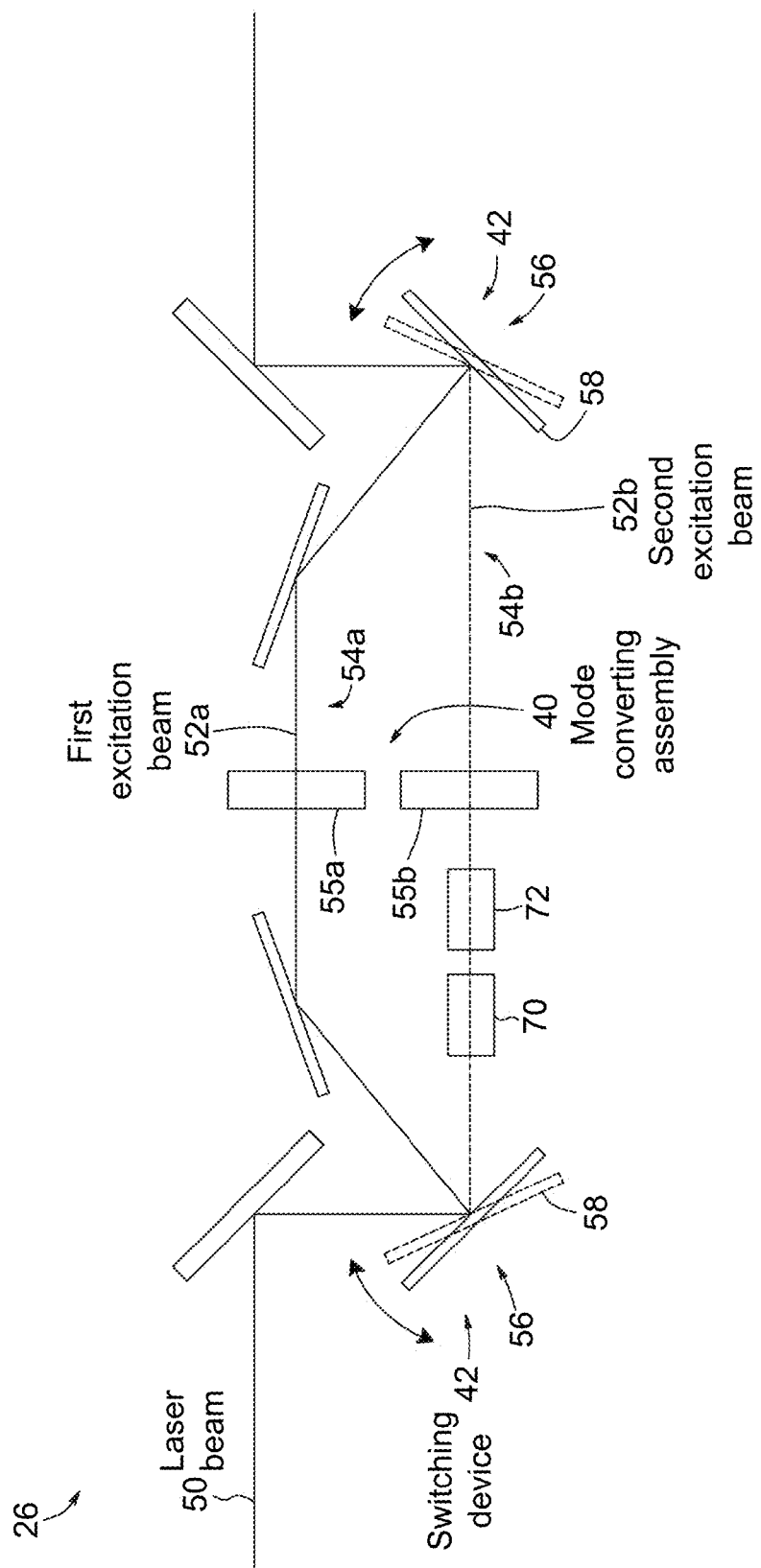
FIG. 11 is a schematic representation of a beam shaping module including a mode converting assembly and a switching device based on rotating mirrors, in accordance with an embodiment of the invention.

FIG. 11 shows a first exemplary embodiment of the beam shaping module 26. In this embodiment, the mode converting assembly 40 of the beam shaping module 26 includes distinct first and second optical paths 54a and 54b respectively associated with the first and second output modes thereof. Each optical path 54a and 54b includes a respective mode converter 55a and 55b that respectively converts the laser beam 50 into the first and second excitation beams 52a and 52b.

Depending on the respective mode profile of the first and second excitation beams 52a and 52b and on performance requirements of the laser imaging system 20, each of the mode converters 55a and 55b of the mode converting assembly 40 may include different optical components or combination of optical components, including a birefringent wave plate assembly, an electro-optic device, a liquid crystal device, fiber a polarization controller, or a combination thereof.

In embodiments such as in FIG. 11 wherein the mode converting assembly 40 includes distinct first and second optical paths 54a and 54b, the switching device 42 preferably includes a beam steering device 56. The beam steering device 56 is adapted to steer the laser beam 50 into the first and second optical paths 54a and 54b of the mode converting assembly 40, so that the respective mode converter 55a and 55b in each of the first and second optical paths 54a and 54b converts the laser beam 50 into the first and second excitation beams 52a and 52b, respectively.

One versatile embodiment of the beam steering device 56 includes at least one rotating mirror 58, each being rotatable between a first position, wherein the laser beam 50 is reflected into the first optical path 54a of the mode converting assembly 40 to be converted into the first excitation beam 52a by the first mode converter 55a, and a second position, wherein the laser beam 50 is reflected into the second optical path 54b of the mode converting assembly 40 to be converted into the second excitation beam 52b by the second mode converter 55b. Preferably, each rotating mirror 58 includes one of a resonant scanning mirror and a galvanomagnetic scanning mirror. It is to be noted that by using Gaussian laser beams with a mirror-based switching device 42, the imaging device 24 can still be used in conventional mode to preserve temporal resolution. For example, using two synchronized mirrors 42, it is possible to switch between different optical paths corresponding to "positive" beam and "negative" beam generation. In this case, there are no more requirements for simultaneous multi-colour applications if the mode converters 55a and 55b include achromatic optical components.

As discussed above, any laser modes having an appropriate intensity profile could be used as the first and second excitation beams. For example, in some embodiments, the first excitation beam may a linearly polarized Gaussian beam, a circularly polarized Gaussian beam or a radially polarized TM beam, while second excitation beam may be a circularly polarized vortex beam or an azimuthally polarized TE beam.

As it is already used in conventional laser scanning microscopes, the linearly polarized Gaussian mode may be the easiest mode to use for the "positive" first excitation beam in some embodiments. Hence, in FIG. 11, it is assumed that in designing the mode converting assembly 40, the laser beam 50 is already linearly polarized. If it is not the case, a polarizer may be placed in the device, as is well known by those of ordinary skill in the art.

As also known in the art, a circularly polarized Gaussian beam may be obtained from a linearly polarized laser beam by using a quarter-wave plate. For multi-colour applications, it could be advantageous to use achromatic or tuneable wave plates, such as stacks of birefringent plates, liquid crystals, or electro-optic components.

A convenient way to produce radially and azimuthally polarized beams from a linearly polarized Gaussian beam is to use a polarization converter, as is well known in the art. In this regard, FIGS. 15A to 15C illustrate the respective paraxial intensity profile and polarization orientation of a linearly polarized Gaussian beam (FIG. 15A), a radially polarized Gaussian beam (FIG. 15B), and an azimuthally polarized beam (FIG. 15C). As shown in FIGS. 15A to 15C, the polarization converter rotates polarization with a different angle depending on the angular position on the beam. For instance, polarization conversion may be done using mosaics (quadrants, octants) of half-wave plates, liquid crystal devices, electro-optic devices, or fiber polarization controllers. Here again, it is advantageous to use achromatic or tuneable wave plates for multi-colour applications.

The generation of radially polarized and azimuthally polarized laser beam can also be done with the superposition of orthogonally polarized $TEM_{01}$ and $TEM_{10}$ laser modes.

The generation of circularly polarized vortex modes is preferably done in two steps. To illustrate this, FIGS. 16A and 16B show the phase of a linearly polarized beam transmitted by two first-order vortex plates. First, a quarter-wave plate is used to get a circularly polarized Gaussian beam. Then a spiral phase shift is used to produce the vortex beam. This phase shift can be applied either in reflection or in transmission (material deposition, holographic methods, liquid crystal, or the like). A tuneable spatial light modulator may also be used.

It will be readily apparent that when the first and second optical paths 54a and 54b are different for the first and second excitation beams 52a and 52b, a z-shift of focal plane could introduced between the two excitation beams. To mitigate this effect, the beam shaping module 26 may preferably including focal-plane-adjusting optics 70 provided along at least one of the first and second optical paths 54a and 54b, and configured for adjusting a shift in position between a focal plane of the first excitation beam 52a and a focal plane of the second excitation beam 52b, as illustrated in FIG. 11.

Figure 12:
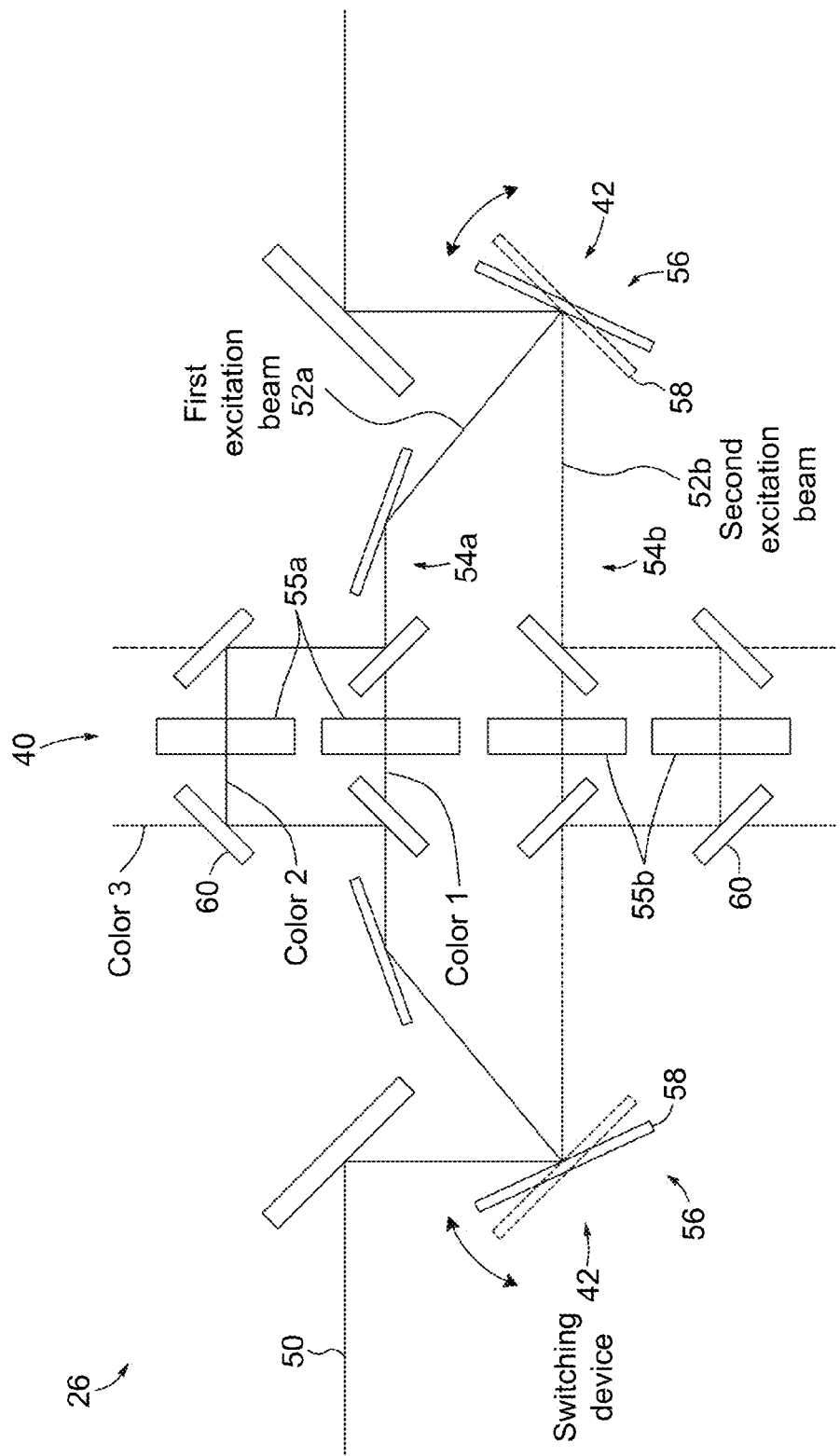
FIG. 12 is a schematic representation of a beam shaping module adapted for simultaneous multi-color applications and including a fixed-wavelength mode converting assembly and a switching device based on rotating mirrors, in accordance with an embodiment of the invention.

When the mode converting assembly 40 includes single-wavelength mode converters 55a and 55b (either fixed or tuneable), sequential multi-colour applications are possible. However, in such cases, a conversion light path per color is required for simultaneous multi-colour applications. In the embodiment of FIG. 12, this is done using dichroic beam splitters 60. In this embodiment, the laser beam 50 includes a plurality of laser beam components, each at a different wavelength, and is received by the beam shaping module 26. As in a FIG. 11, depending on the output mode of the mode converting assembly 40, a rotating mirror 58 of the switching device 42 directs the laser beam 50 into one of the first and second optical paths 54a and 54b mode converting assembly 40. Each of the first and second optical paths 54a and 54b includes a plurality of dichroic beam splitters 60 to separate the laser beam 50 into its beam components (i.e. colors 1, 2 and 3 in FIG. 12). Hence, in the first and second output modes of the mode converting assembly 40, the plurality of beam component of the laser beam 50 are converted by a plurality of mode converters 55a and 55b into a plurality of first and second excitation beam components, respectively. The plurality of first and second excitation beam components are combined into the first and second excitation beams 52a and 52b before exiting the beam shaping module 26.

Figure 13:
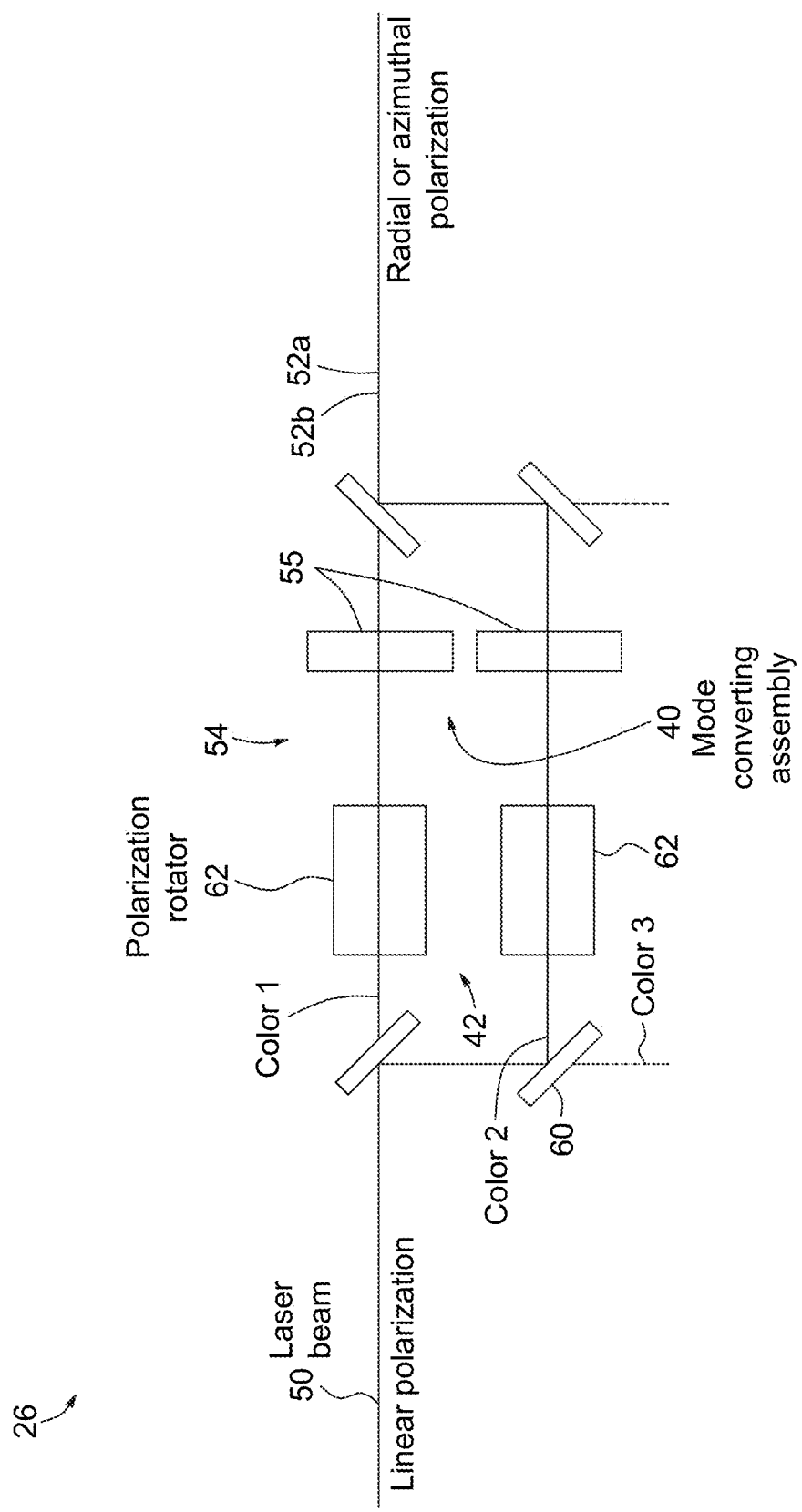
FIG. 13 is a schematic representation of a beam shaping module adapted for simultaneous multi-color applications and including a fixed-wavelength, single-optical-path mode converting assembly and a fixed switching device based on polarization switching between a radially polarized first excitation beam and an azimuthally polarized second excitation beam, in accordance with an embodiment of the invention.

In other embodiments of the beam shaping module 26, such as in FIG. 13, the mode converting assembly 40 includes a same optical path 54 associated with both the first and second output modes. In this embodiment, the mode converting assembly 40 outputs the first and second excitation beams 52a and 52b as a radially polarized TM beam and an azimuthally polarized TE beam, respectively. In this embodiment, the mode converting assembly 40 includes a single optical assembly to produce the first and second excitation beams 52a and 52b, and the switching device 42 exploits the complementarity of radially polarized and azimuthally polarized beams. The switching device 42 includes a polarization rotator 62 disposed between the laser module 22 and the mode converting assembly 40.

The polarization rotator 62 is operable between a first position, in which the linearly polarized laser beam 50 is outputted in a first linear polarization state having a first polarization axis, and a second position, in which the laser beam 50 is outputted in a second linear polarization state having a second polarization axis. The first and second polarization axes of the polarization rotator 62 are orthogonal to each other, so that switching between the first and second output modes of the mode converting assembly 40, that is, between radially and azimuthally polarized excitation beams, is performed by adjusting the polarization rotator 62 between the first and second positions thereof.

In the embodiment of FIG. 13, the switching device 42 can be, for instance, a rotating half-wave plate (achromatic for multi-colour applications), but any device which allows rotating the polarization plane of the incident laser beam 50 by 90 degrees could be used. It could also be advantageous to use tuneable electro-optics (e.g. Pockels cells, liquid crystals or the like) to increase switching speed and suppress all moving parts of the system. For simultaneous multi-colour applications a conversion light path per color may be required if the mode converting assembly 40 does not include achromatic components. As shown in FIG. 13, this may be achieved by using dichroic beam splitters 60.

Figure 14:
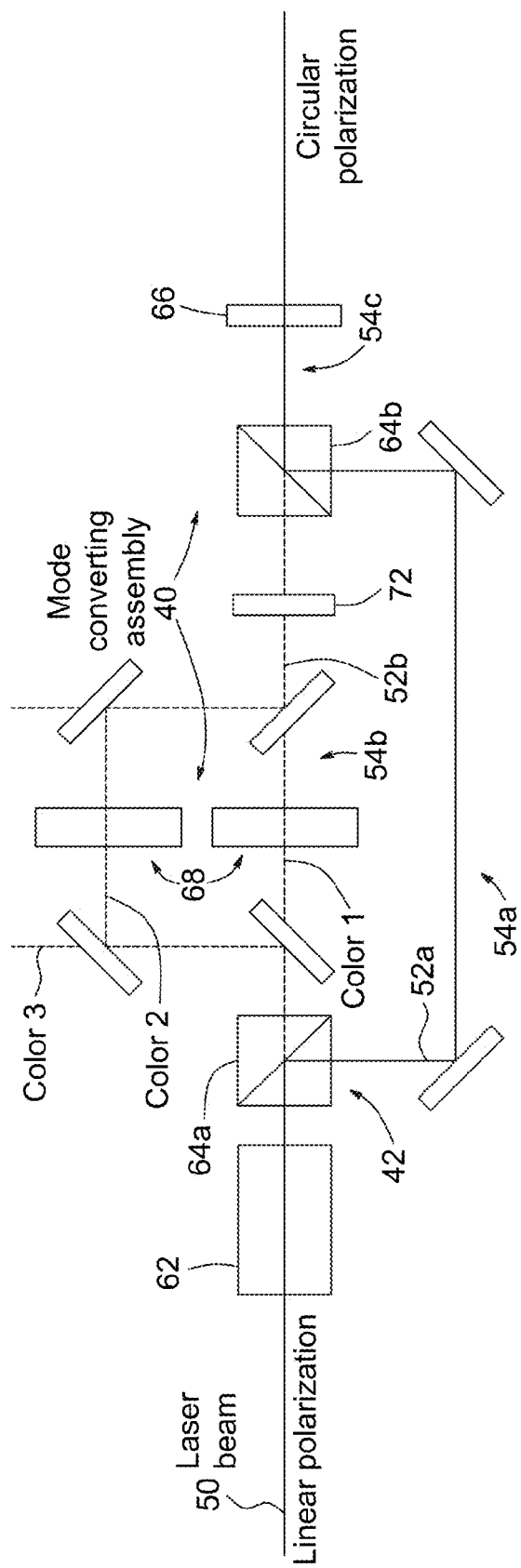
FIG. 14 is a schematic representation of a beam shaping module adapted for simultaneous multi-color applications and including a fixed-wavelength mode converting assembly and a fixed switching device based on polarization switching between a circularly polarized Gaussian first excitation beam and a circularly polarized vortex second excitation beam, in accordance with an embodiment of the invention.

Referring now to FIG. 14, the mode converting assembly 40 outputs both the first and second excitation beams 52a and 52b as circularly polarized beams, and a switching device 42 with no moving parts may be used. The switching device 42 preferably includes a polarization rotator 62 such as described above and polarizing beam splitters 64a and 64b. In the illustrated embodiment, the first polarizing beam splitter 64a is disposed between the polarization rotator 62 and the mode converting assembly 40, while the second polarizing beam splitter 64b is disposed downstream of the first polarizing beam splitter 64a.

By rotating the linear polarization of the incident laser beam 50, the same may be either reflected or transmitted by the first polarizing beam splitter 64a into the first or second optical paths 54a and 54b of the mode converting assembly 40. A vortex plate 68 (e.g. a first-order vortex plate) embodying part of the mode converting assembly 40 may be disposed along the second optical path 54b to generate a linearly polarized second excitation beam. The first and second optical paths 54a and 54b merge together again into a common optical path 54c after the second polarizing beam splitter 64b, where the mode converting assembly 40 further includes a quarter-wave plate 66 to obtain a circularly polarized Gaussian beam for the first excitation beam 52a and a circularly polarized vortex beam for the second excitation beam 52b. The common optical path 54c directs the first and second excitation beams 52a and 52b toward the imaging device of the laser imaging system. For simultaneous multi-colour application without achromatic mode converters, a conversion light path per color is required and an achromatic quarter-wave 66 plate can be used. As shown in FIG. 13, this again can be achieved by using dichroic beam splitters 60.

It is to be noted that the embodiments illustrated in FIGS. 11 to 14 are all compatible with both continuous wave and pulsed lasers. In addition, for nonlinear laser scanning microscopy requiring unchirped short pulses, a dispersion compensator could be added to the laser imaging system, as would be apparent to one of ordinary skill in the art.

Furthermore, the beam steering device 56 (e.g. rotating mirrors) and the polarization rotator 62 may conveniently be retrofitted into an existing laser scanning microscope since scanning signal and laser beams are accessible. To further facilitate integration of the beam shaping module 26 into the laser scanning imaging system 20, such as the one of FIG. 11, a fiber-based and a free-space-based version of the beam shaping module 26 may be provided depending on the link between the scanning module 48 (e.g. scan head) of the imaging device 24 and the laser module 22.

Another way to produce and switch between "positive" first and "negative" second excitation beams is to generate the same inside the laser cavity of the laser module 22.

Figure 17B:
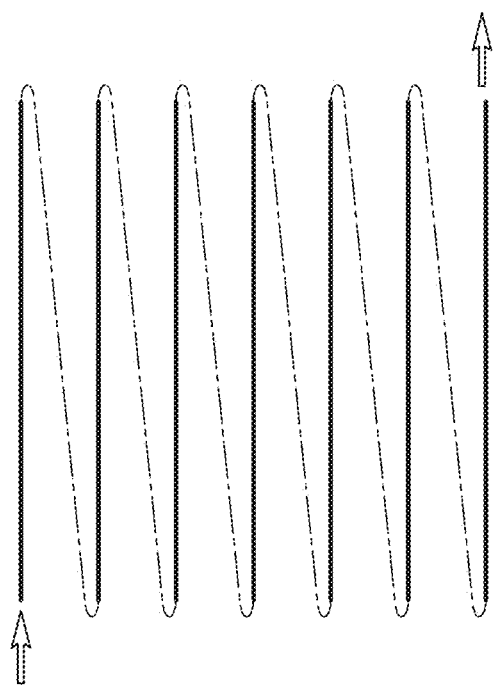
FIGS. 17A and 17B illustrate a sawtooth scan of a specimen without (FIG. 17A) and with (FIG. 17B) image subtraction.
Figure 17A:
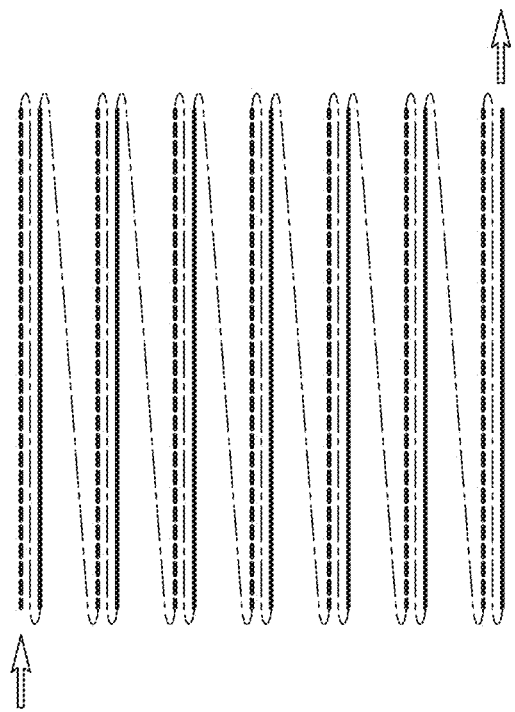

Furthermore, in embodiments of the invention where fast acquisition may be required, it could be advantageous to use fast switching devices 42 such as resonant scanners or galvanometer mirrors for the rotating mirrors 58 (see FIGS. 11 and 12) and Pockels cells for the polarization rotator 62 (see FIGS. 13 and 14). In this regard, in embodiments of the laser imaging system 20 that include a scanning module 48 (see FIG. 4), it could also be advantageous to synchronize switching by the switching device 42 and sample scanning by the scanning module 48 to record data directly with software of the imaging device 24. Preferably, switching dwell-time is at least lower than the dwell-time of the backward movement of the scanning module 48 (see, e.g. the long-dash-short-dash in FIGS. 17A and 17B). For sawtooth scans, FIGS. 17A and 17B illustrate that obtaining an image of the specimen using the method according to embodiments of the present invention (FIG. 17B), that is with a positive (solid line) and a negative scanning line (dashed line), requires twice the time needed to obtain an image with a single scanning line (FIG. 17A). For this reason, one of ordinary skill in the art will understand that some embodiments of the present invention could benefit from the use of fast switching devices 42.

As is well known in the art, laser beams can be affected in intensity and phase by dielectric coatings present inside the imaging device (e.g. in dichroic mirrors, dielectric mirrors, filters, and the like). This may produce distortions of the laser beams at focus and reduce the performances of the laser imaging system. More particularly, when radially, circularly or azimuthally polarized light is used, as in some embodiments of the invention, various polarization states are present in excitation beams. Because s-polarization and p-polarization are not always transmitted/reflected by dielectrics coatings with the same phase and transmission/reflection ratio, polarization may be affected before being focused onto the volume of the sample by the objective lens of the imaging device. As a result, the shape of the focal spot may change. To help mitigating such polarization-dependent effects, it may be possible, in some embodiments, to pre-compensate for phase and intensity distortions by introducing a pre-compensation module 72, for example one or more correction plates, in the beam shaping module 26 (see, e.g., FIGS. 11 and 14). The intensity correction plates may be embodied by a pellicle beam splitter or a pair wedge prisms. As will be readily understood by one of ordinary skill in the art, the transmission and reflection ratios of s-polarization and p-polarization may be controlled by adjusting the relative angle between the optical axis of the excitation beam and the pellicle beam splitter or the wedge prism. More particularly, for a specific orientation, intensity distortions may be pre-compensated for. Phase distortions may also be pre-compensated for by using a set of half-wave and quarter-wave plates. Alternatively or additionally, spatial light modulators may be used to compensate simultaneously phase and intensity distortions. Any other programmable phase or intensity modulators could also be used.

In configurations such as in FIG. 11 where the mode converter includes distinct first and second optical paths associated with the first and second output modes, the pre-compensation module 72 may be disposed in an optical path 54a and 54b of at least one of the first and second excitation beams 52a and 52b for pre-compensating for polarization-dependent phase and intensity distortions affecting at least one of the first and second excitation beams 52a and 52b while propagating within the imaging device.

Experimental Demonstration

An experimental demonstration illustrating the resolution enhancement capabilities provided by the present invention will now be considered. As one of ordinary skill in the art will readily understand, embodiments of the present invention are not limited to this particular experimental demonstration.

FIGS. 18A and 18B show two experimental examples of resolution enhancement in confocal imaging. In both cases, a 1.2 numerical aperture objective and a contrast enhancing module have been used. The excitation wavelength was 532 nm. No deconvolution was used.

In FIG. 18A, a first example compares conventional confocal images with high-resolution images of dendritic spines of m-Ruby-transfected cultured neurons. A reduction of the full width at half maximum of the imaged structure by a factor of 3.4 is obtained when applying the method described above.

In FIG. 18B, a second example makes the same comparison with neuronal growth cones, where details were revealed by immunohistochemical labeling of tubulin. Using conventional confocal imaging, images are blurry and close structures cannot be distinguished whereas those structures are well separated when using the high-resolution subtraction method described above.

Of course, numerous modifications could be made to the embodiments described above without departing from the scope of the present invention.

The invention claimed is:

1. A method for obtaining a high-resolution image of a volume of a sample using laser imaging, the method comprising the steps of:
   (a) probing the volume of the sample with a first excitation beam having an intensity profile of maximum intensity at a center thereof, the first excitation beam inducing a first emission of electromagnetic radiation from said volume; and obtaining a positive image of said volume by sensing said first emission of electromagnetic radiation;
   (b) at a time when the first excitation beam is not active, probing the volume of the sample with a second excitation beam having an intensity profile of minimum intensity at a center thereof and defining a peripheral region of maximum intensity around said center, the second excitation beam inducing a second emission of electromagnetic radiation from said volume; and obtaining a negative image of said volume by sensing said second emission of electromagnetic radiation, said negative image being distinct from said positive image; and
   (c) subtracting the negative image from the positive image, thereby obtaining said high-resolution image of said volume of the sample.

2. The method according to claim 1, wherein step (a) comprises using, as the first excitation beam, one of a linearly polarized Gaussian beam, a circularly polarized Gaussian beam and a radially polarized transverse magnetic beam.

3. The method according to claim 1, wherein step (b) comprises using, as the second excitation beam, one of a circularly polarized vortex beam and an azimuthally polarized transverse electric beam.

4. The method according to claim 1, further comprising, prior to step (c), a step of multiplying an intensity of at least one of the positive and negative images by a scaling factor.

5. The method according to claim 1, wherein:
   step (a) comprises directing a plurality of first excitation beam components onto the sample in a manner such that the plurality of first excitation beam components spatially and temporally overlap with one another to form the first excitation beam at the volume of the sample; and
   step (b) comprises directing a plurality of second excitation beam components onto the sample in a manner such that the plurality of second excitation beam components spatially and temporally overlap with one another to form the second excitation beam at the volume of the sample.

6. The method according to claim 1, further comprising:
   selecting a plurality of excitation wavelengths; and
   performing steps a) to c) for a plurality of acquisition cycles, the first and second excitation beams having a different one of the plurality of excitation wavelengths for each of said acquisition cycles.

7. A method for obtaining a combined high-resolution image of a sample comprising a plurality of volumes using laser imaging, the method comprising the steps of:
   i) performing the method according to claim 1 for each of the plurality of volumes of the sample, thereby obtaining a corresponding plurality of high-resolution images; and
   ii) combining the plurality of high-resolution images to form the combined high-resolution image of the sample.

8. The method according to claim 7, wherein step i) comprises scanning the first and second excitation beams over the plurality of volumes of the sample.

9. A laser imaging system for obtaining a high-resolution image of a volume of a sample, the laser imaging system comprising:
   a laser module configured to generate a laser beam;
   a beam shaping module comprising:
      a mode converting assembly comprising a first output mode in which the mode converting assembly is configured to convert the laser beam into a first excitation beam having an intensity profile of maximum intensity at a center thereof, and a second output mode in which the mode converting assembly is configured to convert the laser beam into a second excitation beam having an intensity profile of minimum intensity at a center thereof and defining a peripheral region of maximum intensity around said center; and
      a switching device configured to switch between said first and second output modes of the mode converting assembly in order to output, one at a time, the first and second excitation beams to probe the volume of the sample;
   an imaging device configured to image the volume of the sample, the imaging device being configured to, when the mode converting assembly is in the first output mode, propagate the first excitation beam to the volume of the sample, the first excitation beam inducing a first emission of electromagnetic radiation from said volume, and acquire a positive image of said volume of the sample by sensing said first emission of electromagnetic radiation, the imaging device being configured to, when the mode converting assembly is in the second output mode, propagate the second excitation beam to the volume of the sample, the second excitation beam inducing a second emission of electromagnetic radiation from said volume, and acquire a negative image of said volume of the sample by sensing said second emission of electromagnetic radiation, said negative image being distinct from said positive image; and a processor configured to subtract the negative image from the positive image, thereby obtaining said high-resolution image of said volume of the sample.

10. The laser imaging system according to claim 9, wherein the first excitation beam comprises one of a linearly polarized Gaussian beam, a circularly polarized Gaussian beam and a radially polarized transverse magnetic beam.

11. The laser imaging system according to claim 9, wherein the second excitation beam comprises one of a circularly polarized vortex beam and an azimuthally polarized transverse electric beam.

12. The laser imaging system according to claim 9, wherein the imaging device is one of a confocal microscope, a one-photon excitation microscope, a multi-photon excitation microscope, a second-harmonic imaging microscope, a third-harmonic imaging microscope, a reflectance microscope, a coherent anti-Stokes Raman scattering system, a stimulated Raman scattering system and a sum-frequency generation system.

13. The laser imaging system according to claim 9, wherein the imaging device is a two-photon excitation microscope.

14. The laser imaging system according to claim 9, wherein the imaging device comprises:

imaging optics configured to receive either one of the first and second excitation beams from the beam shaping module and to focus the same onto the volume of the sample; and an image sensor sensing the first and second emissions of electromagnetic radiation emanating from the volume of the sample upon being probed by the first and second excitation beams and producing therefrom the positive and negative images of said volume, respectively.

15. The laser imaging system according to claim 14, wherein the imaging device further comprises a scanning module configured to scan the first and second excitation beams over a plurality of volumes of the sample so as to obtain a corresponding plurality of pairs of positive and negative images, the processor being further configured to subtract the negative image of each of said pairs from the respective positive image, thereby obtaining said high-resolution image for each of said volumes of the sample.

16. The laser imaging system according to claim 9, wherein the beam shaping module is one of integrated into the laser module, integrated into the imaging device, and separated from and disposed between the laser module and the imaging device.

17. The laser imaging system according to claim 9, wherein the mode converting assembly comprises at least one of a birefringent wave plate assembly, an electro-optic device, a liquid crystal device and a fiber polarization controller.

18. The laser imaging system according to claim 9, wherein:

the mode converting assembly comprises distinct first and second optical paths respectively associated with the first and second output modes thereof, each optical path comprising a respective mode converter, and the switching device comprises a beam steering device adapted to steer the laser beam into the first and second optical paths of the mode converting assembly, so that the respective mode converter in each of the first and second optical paths converts the laser beam into the first and second excitation beams, respectively.

19. The laser imaging system according to claim 18, wherein the beam steering device comprises at least one rotating mirror.

20. The laser imaging system according to claim 19, wherein each rotating mirror comprises one of a resonant scanning mirror and a gaivanomagnetic scanning mirror.

21. The laser imaging system according to claim 18, wherein:

the mode converting assembly outputs the first and second excitation beams as a circularly polarized Gaussian beam and a circularly polarized vortex beam, respectively;

the switching device comprises a polarization rotator disposed between the laser module and the mode converting assembly, the polarization rotator being configured to operate between a first position, in which the laser beam is outputted in a first linear polarization state having a first polarization axis, and a second position, in which the laser beam is outputted in a second linear polarization state having a second polarization axis orthogonal to the first polarization axis, so that switching between the first and second output modes of the mode converting assembly is performed by adjusting the polarization rotator between the first and second positions thereof; and the beam steering device of the switching device comprises:

a first polarizing beam splitter disposed between the polarization rotator and the mode converting assembly and configured to transmit one of the first and second linear polarization states associated with the polarization rotator into one of the first and second optical paths of the mode converting assembly, and to reflect the other one of the first and second linear polarization states associated with the polarization rotator into the other one of the first and second optical paths of the mode converting assembly; and a second polarizing beam splitter disposed downstream of the first polarizing beam splitter and configured to merge the first and second optical paths of the mode converting assembly into a common optical path.

22. The laser imaging system according to claim 18, wherein the beam shaping module further comprises focal-plane-adjusting optics provided along at least one of the first and second optical paths and configured to adjust a shift in position between a focal plane of the first excitation beam and a focal plane of the second excitation beam.

23. The laser imaging system according to claim 9, wherein:

the mode converting assembly comprises a same optical path associated with both the first and second output modes, and outputs the first and second excitation beams as a radially polarized transverse magnetic beam and an azimuthally polarized transverse electric beam, respectively;

the switching device comprises a polarization rotator disposed between the laser module and the mode converting assembly, the polarization rotator being configured to operate between a first position, in which the laser beam is outputted in a first linear polarization state having a first polarization axis, and a second position, in which the laser beam is outputted in a second linear polarization state having a second polarization axis orthogonal to the first axis, so that switching between the first and second output modes of the mode converting assembly is performed by adjusting the polarization rotator between the first and second positions thereof.

24. The laser imaging system according to claim 9, wherein the processor comprises a contrast-enhancing module multiplying an intensity of at least one of the positive and negative images by a scaling factor prior to subtracting the negative image from the positive image.

25. The laser imaging system according to claim 9, wherein the laser module comprises a plurality of laser sources configured to emit a corresponding plurality of beam components, each at a different wavelength, at least one of the beam components being used to generate the laser beam.

26. The laser imaging system according to claim 9, further comprising a pre-compensation module disposed in a path of at least one of the first and second excitation beams, the pre-compensation module being configured to pre-compensate for polarization-dependent phase and intensity distortions affecting at least one of the first and second excitation beams while propagating within the imaging device.

* * * * *